(12) United States Patent
Ades et al.

(10) Patent No.: US 6,903,184 B1
(45) Date of Patent: Jun. 7, 2005

(54) **MULTIPLE ANTIGENIC PEPTIDES IMMUNOGENIC AGAINST *STREPTOCOCCUS PNEUMONIA***

(75) Inventors: Edwin W. Ades, Atlanta, GA (US); Scott E. Johnson, Lilburn, GA (US); Danny L. Jue, Tucker, GA (US); Jacquelyn S. Sampson, College Park, GA (US); George M. Carlone, Stone Mountain, GA (US)

(73) Assignee: The United States of America as represented by the Secretary of the Department of Health and Human Services, Washington, DC (US)

(*) Notice: Subject to any disclaimer, the term of this patent is extended or adjusted under 35 U.S.C. 154(b) by 515 days.

(21) Appl. No.: 09/613,092

(22) Filed: Jul. 10, 2000

Related U.S. Application Data

(63) Continuation-in-part of application No. PCT/US99/04326, filed on Feb. 26, 1999, now abandoned.
(60) Provisional application No. 60/076,565, filed on Mar. 2, 1998.

(51) Int. Cl.[7] .............................. C07K 2/00; C07K 5/00; C07K 1/00; A61K 39/09; A61K 39/02
(52) U.S. Cl. ........................ 530/300; 530/350; 530/323; 530/825; 530/331; 530/806; 514/2; 424/244.1; 424/234.1; 424/190.1; 424/184.1
(58) Field of Search .............................. 514/2; 530/350, 530/300, 825, 331, 323, 806; 424/184.1, 190.1, 244.1, 234.1

(56) References Cited

U.S. PATENT DOCUMENTS

| | | | |
|---|---|---|---|
| 5,422,427 A | 6/1995 | Russell et al. | ............... 530/350 |
| 5,854,416 A | 12/1998 | Sampson et al. | ........... 536/23.7 |
| 6,217,884 B1 * | 4/2001 | Sampson et al. | ........ 442/266.1 |

FOREIGN PATENT DOCUMENTS

| | | |
|---|---|---|
| WO | WO 91/17258 * | 11/1991 |
| WO | WO 99/40200 A | 8/1999 |
| WO | WO 99/45121 | 9/1999 |
| WO | WO 99/45121 A | 9/1999 |

OTHER PUBLICATIONS

Srivastava et al. Hybridoma 19: 23–31, 2000.*
Harlow et al. In: Antibodies: A Laboratory Manual. Cold Spring Harbor Laboratory, Chapter 5, p. 76, 1988.*
Tam et al. In: Peptide Antigens: A Practical Approach. (Ed) Wisdom GB. IRL Press, Oxford University Press, New York, pp. 83–90, 1993.*
Huang et al. Mol. Immunol. 31: 1191–1199, 1994.*
De et al. Pathobiology 67: 115–122, May–Jun. 1999.*
Morrison, K.E. et al., "Confirmation of psaA in All 90 Serotypes of *Streptococcus pneumoniae* by PCR and Potential of This Assay for Identification and Diagnosis," *Journal of Clinical Microbiology* 38(1):434–437 (2000).

Sampson, Jacquelyn S. et al, "Limited Diversity of *Streptococcus pneumoniae* psaA among Pneumococcal Vaccine Serotypes," *Infection and Immunity* 65:1967–1971 (1997).
Srivastava, N. et al., "Selection of an Immunogenic and Protective Epitope of the PsaA Protein of *Streptococcus pneumoniae* Using a Phage Display Library," *Hybridoma* 19(1):23–31 (2000).
Verhuel, A.F.M., et al., "Monopalmitic acid–peptide conjugates induce cytotoxic T cell responses against malarial epitopes: importance of spacer amino acids", *Journal of Immunological Methods*, 182 (1995), pp. 219–2216.
Srivastava, N., et al., "Selection of an Immunogenic and Protective Eptiope of the PsaA Protein of *Streptococcus pneumoniae* Using a Phage Display Library", *Hybridoma*, vol. 19, No. 1, 2000.
Sampson, J. S., et al. "Cloning and Nucleotide Sequence Analysis of PsaA, the *Streptococcus pneumoniae* Gene Encoding a 37–Kilodalton Protein Homologous to Previously Reported *Streptococcus* sp. Adhesins", *Infection and Immunity*, Jan. 1994, p. 319–324.
Russell, H., et al., "Monoclonal Antibody Recognizing a Species–Specific Protein from *Streptococcus pneumoniae*", Journal of Clinical Microbiology, Oct. 190, pp. 2191–2195.
Tharpe, J. A., et al., Purification and Seroreactivity of Pneumococcal Surface Adhesin A (PsaA), *Clinical and Diagnostic Laboratory Immunology*, Mar. 1996, p. 227–229.
Talkington et al., "Protection of mice against fat pneumococcal challenge by immunization with pneumonococcal surface adhesin A (PsaA)", Microbiol. Pathogenesis, 21:17–22.
Tharpe et al., "The utility of a recombinant protein in an enzyme immunoassay for antibodies against *Streptococcus pneumoniae*", Abstract V–2, p. 617, 1994, American Society for Microbiology, Washington, D.C.

* cited by examiner

Primary Examiner—S. Devi
(74) Attorney, Agent, or Firm—Needle & Rosenberg, P.C.

(57) ABSTRACT

The invention provides a nucleic acid encoding the 37-kDa pneumococcal surface adhesion A protein (PsaA) from *Streptococcus pneumoniae*. The invention also provides purified polypeptides encoded by the nucleic acid encoding the 37-kDa protein from and the nucleic acids comprising unique fragment of at least 10 nucleotides of the 37-kDa protein. Additionally, multiple antigenic peptides that provide protection against *S. pneumoniae* challenge are provided. These multiple antigen peptides comprise the peptides that immunospecifically bind to the monoclonal antibodies. Also provided are vaccines comprising such immunogenic peptides, and methods of conferring protective immunity against *Streptococcus pneumoniae* infection by administering therapeutic composition comprising the immunogenic peptides of the invention. Also provided are methods of detecting the presence of *Streptococcus pneumoniae* in a sample using antibodies or antigens and methods of preventing and treating *Streptococcus pneumoniae* infection in a subject.

1 Claim, 1 Drawing Sheet

Amino terminal        Carboxy terminal

FIG. 1A

TVSRVPWTAWAFHGY⟍
                   ⟩K-Nle⟍
SYQHDLRAYGFWRL╱          ⟍
                          K-Nle
TVSRVPWTAWAFHGY⟍        ╱
                ⟩K-Nle╱
SYQHDLRAYGFWRL╱

FIG. 1B

TVSRVPWTAWAFHGY⟍
                ⟩K-Nle⟍
LVRRFVHRPHVESQ╱        ⟍
                        K-Nle
TVSRVPWTAWAFHGY⟍       ╱
                ⟩K-Nle╱
LVRRFVHRPHVESQ╱

FIG. 1C

TVSRVPWTAWAFHGY⟍
                ⟍
SYQHDLRAYGFWRL⟍   K-Nle
               ⟍  ╱
                K-Nle
LVRRFVHRPHVESQ╱

MULTIPLE ANTIGENIC PEPTIDES IMMUNOGENIC AGAINST STREPTOCOCCUS PNEUMONIA

This application is a continuation-in-part of Application No. PCT/US99/04326, filed Feb. 26, 1999, now abandoned, which claims the benefit of U.S. Provisional Application No. 60/076,565, filed Mar. 2, 1998, now abandoned.

FIELD OF THE INVENTION

This invention relates to preventing infection by *Streptococcus pneumoniae*. More specifically, the invention relates to peptides derived from a peptide library that are related to the *S. pneumoniae* pneumococcal surface adhesion A protein (PsaA) and that are immunogenic in a subject. The invention also relates to pharmaceutical and therapeutic compositions containing these peptide fragments and methods of conferring protection against infection by *S. pneumoniae*. Even more specifically, this invention relates to multiple antigenic peptides immunogenic against *Streptococcus pneumoniae*.

BACKGROUND OF THE INVENTION

Pneumococcal disease continues to be a leading cause of sickness and death in the United States and throughout the world. The currently used polysaccharide vaccines have limited efficacy in children under 2 years of age and exhibit variable serotype-specific efficacy among vaccinated individuals. For these reasons, alternative vaccine formulations have been investigated that do not require the use of multiple capsular polysaccharides. One current approach under consideration is the use of immunogenic species-common proteins as vaccine candidates. These proteins could be used in combination with other immunogenic proteins or as protein carriers in a protein, polysaccharide, or oligosaccharide conjugate vaccine. An effective vaccine that includes a common protein could eliminate the need for formulations based on multiple capsular polysaccharides (as in the current 23-valent polysaccharide vaccine) by offering a broader range of protection against a greater number of serotypes. Additionally, a protein-based vaccine would be T-cell dependent and provide a memory response, thereby resulting in a more efficacious vaccine.

An immunogenic species-common protein has been identified from *Streptococcus pneumoniae* (Russell et al., 1990, "Monoclonal antibody recognizing a species-specific protein from *Streptococcus pneumoniae*." *J. Clin. Microbiol.*, 28:2191–2195; and U.S. Pat. No. 5,422,427). A 37-kDa *S. pneumoniae* protein has been the focus of several studies and is now designated pneumococcal surface adhesin protein A (PsaA). (This 0.37-kDa protein was referred to as pneumococcal fimbrial protein A in U.S. Pat. No. 5,422,427; the terms are used interchangeably in the present specification.) Immunoblot analysis studies using anti-PsaA monoclonal antibody showed that PsaA is common to all 23 pneumococcal vaccine serotypes (Russell et al., 1990). Enzyme-linked-immunosorbent assay studies have indicated that patients with pneumococcal disease show an antibody increase in convalescent-phase serum to PsaA compared with acute-phase serum antibody levels (Tharpe et al., 1995, "Purification and seroreactivity of pneumococcal surface adhesin A (PsaA)," *Clin. Diagn. Lab. Immunol.* 3:227–229; and Tharpe et al., 1994, "The utility of a recombinant protein in an enzyme immunoassay for antibodies against *Streptococcus pneumoniae*," Abstr. V-2, p 617, 1994, American Society for Microbiology, Washington, D.C.). Additionally, a limited in vivo protection study showed that antibodies to the 37-kDa protein protect mice from lethal challenge. (Talkington et al., 1996, "Protection of mice against fatal pneumococcal challenge by immunization with pneumococcal surface adhesin A (PsaA)," *Microbial Pathogenesis* 21:17–22). The gene encoding PsaA from *S. pneumoniae* strain R36A (an unencapsulated strain) has been cloned in *Escherichia coli* and sequenced; this strain, however, does not contain a 37-kDa protein encoding nucleic acid that is highly conserved among the various serotypes, (Sampson et al., 1994, "Cloning and nucleotide sequence analysis of PsaA, the *Streptococcus pneumoniae* gene encoding a 37-kilodalton protein homologous to previously reported *Streptococcus* sp. adhesins," *Infect. Immun.* 62:319–324). This particular nucleic acid and the corresponding polypeptide, therefore, are of limited value for use as diagnostic reagents, in preventing infection, in treating infection, or in vaccine development. In U.S. patent application Ser. No. 08/715,131, filed Sep. 17, 1996, (now U.S. Pat. No. 5,854,416) which is a continuation-in-part of U.S. patent application Ser. No. 08/222,179, filed Apr. 4, 1994, which is a continuation-in-part of U.S. patent application Ser. No. 07/791,377, filed Sep. 17, 1991 (now U.S. Pat. No. 5,422,427), all of which are hereby incorporated by reference in their entirety, an isolated nucleic acid encoding the 37-kDa protein of *Streptococcus pneumoniae*, unique fragments of at least 10 nucleotides of this nucleic acid which can be used in methods to detect the presence of *Streptococcus pneumoniae* in a sample and as immunogenic vaccines have been disclosed. Furthermore, a purified polypeptide encoded by this nucleic acid, encoding the 37-kDa protein of *Streptococcus pneumoniae*, which can be used in immunogenic vaccines, has been disclosed. Additionally, purified antibodies which bind to the 37-kDa protein of *Streptococcus pneumoniae* or fragments thereof, which can be used in methods to detect the presence of *Streptococcus pneumoniae*, and in therapeutic and prophylactic methods, have been disclosed. Sequence conservation is a necessary requirement for a candidate species-common vaccine. The sequence conservation of the PsaA gene among pneumococcal types, and specifically among encapsulated pneumococci which cause the vast majority of cases of serious disease, remains under investigation. There exists a need to identify characteristic epitopes related to *S. pneumoniae* PsaA in order to provide polypeptides which can serve as a vaccine for multiple strains of *Streptococcus pneumoniae*. The present invention addresses this need by determining effective epitopic peptides related to *S. pneumoniae* PsaA, and employing those peptides in therapeutic compositions directed against *Streptococcus pneumoniae* infection.

SUMMARY OF THE INVENTION

The present invention describes novel immunogenic peptides obtained from a random library by selecting for high affinity binding to monoclonal antibodies specific for PsaA epitopes. In addition, the peptides of the invention have the capability of serving as immunogens in a subject, thereby effectively eliciting the production of antibodies by the subject and additionally conferring protective immunity against infection by *S. pneumoniae* on the subject. The invention also relates to a selection method employed to obtain such peptides.

The peptides of the invention include peptides comprising residues whose sequence is chosen from the group consisting of SEQ ID NO:5, SEQ ID NO:6, SEQ ID NO:7, SEQ ID NO:8, SEQ ID NO:9, SEQ ID NO.10, and immunogenic fragments thereof. In certain embodiments, the peptides consist essentially of a sequence selected from SEQ ID NO:5, SEQ ID NO:6, SEQ ID NO:7, SEQ ID NO:8, SEQ ID NO:9, SEQ ID NO.10, and immunogenic fragments thereof. In certain embodiments the peptides consist of a sequence selected from SEQ ID NO:5, SEQ ID NO:6, SEQ ID NO:7, SEQ ID NO:8, SEQ ID NO:9, SEQ ID NO.10, and immunogenic fragments thereof.

The invention additionally provides peptides as described above, wherein the peptides are multiple antigenic peptides. In one embodiment, the multiple antigenic peptide has at least one arm comprising a sequence selected from SEQ ID NO:5, SEQ ID NO:6, SEQ. ID. NO:7, SEQ ID NO:8, SEQ ID NO:9, SEQ ID NO.10, and immunogenic fragments thereof. In another embodiment, the multiple antigenic peptide has at least one arm consisting essentially of a sequence selected from SEQ ID NO:5, SEQ ID NO:6, SEQ ID NO:7, SEQ ID NO:8, SEQ ID NO:9, SEQ ID NO.10, and immunogenic fragments thereof. In-another embodiment, the multiple antigenic peptide has at least one arm consisting of a sequence selected from SEQ ID NO:5, SEQ ID NO:6, SEQ. ID NO:7, SEQ ID NO:8, SEQ ID NO:9, SEQ ID NO.10, and immunogenic fragments thereof.

In one embodiment, the multiple antigenic peptide has at least one first arm comprising SEQ ID NO:5 and at least one second arm comprising SEQ ID NO:6. In another embodiment, the multiple antigenic peptide has at least one first arm comprising SEQ ID NO:5 and at least one second arm comprising SEQ ID NO:7. In another embodiment, the multiple antigenic peptide has at least one first arm comprising SEQ ID NO:5 and at least one second arm comprising SEQ ID NO:9. In another embodiment, the multiple antigenic peptide has at least one first arm comprising SEQ ID NO:6 and at least one second arm comprising SEQ ID NO:7. In another embodiment, the multiple antigenic peptide has at least one first arm comprising SEQ ID NO:10 and at least one second arm comprising SEQ ID NO:9. In yet another embodiment, the multiple antigenic peptide has at least one first arm comprising SEQ ID NO:10 and at least one second arm comprising SEQ ID NO:7. In still another embodiment, the multiple antigenic peptide has at least one first arm comprising SEQ ID NO:5 and at least one second arm comprising SEQ ID NO:10. In another embodiment, the multiple antigenic peptide has at least one first arm comprising SEQ ID NO:6 and at least one second arm comprising SEQ ID NO:7. In another embodiment, the multiple antigenic peptide has at least one first arm comprising SEQ ID NO:5, at least one second arm comprising SEQ ID NO:6, and at least one third arm comprising SEQ ID NO:7. In another preferred embodiment, the multiple antigenic peptide has at least one first arm comprising SEQ ID NO:5, at least one second arm comprising SEQ ID NO:9, and at least one third arm comprising SEQ ID NO:10.

In another aspect, the current invention is a peptide that immunospecifically binds to a monoclonal antibody obtained in response to immunizing an animal with *Streptococcus pneumoniae* PsaA, wherein the peptide is lipidated. In one embodiment, the peptide is lipidated with monopalmitic acid.

The invention furthermore provides a therapeutic composition in which the immunogenic peptides are combined with an immunostimulatory carrier to be administered to a subject in order to elicit an immune response which confers protective immunity against infection by *S. pneumoniae* on the subject.

The invention additionally provides a therapeutic composition in which the immunogenic peptides are combined with an adjuvant to be administered to a subject in order to elicit an immune response which confers protective immunity against infection by *S. pneumoniae* on the subject.

The invention additionally provides a therapeutic composition in which the immunogenic peptide is multiple antigenic peptide of the current invention as described above.

The invention additionally provides a therapeutic composition in which the immunogenic peptide is a peptide that immunospecifically binds to a monoclonal antibody obtained in response to immunizing an animal with *Streptococcus pneumoniae* PsaA, wherein the peptide is lipidated. In one embodiment, the peptide is lipidated with monopalmitic acid.

The invention still further describes a method of conferring protective immunity against infection by *S. pneumoniae* on a subject in which the therapeutic compositions of the invention are administered to the subject.

A further aspect of the invention presents a method for identifying a peptide incorporating PsaA or a fragment thereof (i.e., an immunogenic peptide) that elicits an immunogenic response in a subject directed against *S. pneumoniae*. The method entails preparing a random peptide library, screening the peptide library in order to identify immunogenic peptides, and obtaining the amino acid sequence of the immunogenic peptide.

The advantages of the invention will be realized and attained by means of the elements and combinations particularly pointed out in the appended claims. It is to be understood that both the foregoing general description and the following detailed description are exemplary and explanatory only and are not restrictive of the invention, as claimed. Throughout this application, various publications are referenced. The disclosures of these publications in their entireties are hereby incorporated by reference into this application in order to more fully to describe the state of the art to which this application pertains.

BRIEF DESCRIPTION OF THE DRAWINGS

FIG. 1 contains diagrams of the multi-antigenic peptides (MAPS) of the current invention. FIG. 1A shows a bi-peptide heterogeneous MAP with arms of alternating peptides with sequences of either SEQ ID NO:5 or SEQ ID NO:6. FIG. 1B shows a bi-peptide heterogeneous MAP with arms of alternating peptides with sequences of either SEQ ID NO:5 or SEQ ID NO:9. FIG. 1C shows a tri-peptide heterogeneous MAP with a first arm with the sequence of SEQ ID NO:5, a second arm with the sequence of SEQ ID NO:10, and a third arm with the sequence of SEQ ID NO:9. The carboxy terminal lysine (i.e., K) residue in each peptide is shared between two arms of the MAP. Nle is norleucine.

DETAILED DESCRIPTION OF THE INVENTION

As used herein, "immunogenic peptide" refers to a peptide which, upon being administered to a subject, or taken up by the subject in other ways, elicits an immune response. The immune response includes at least the generation of antibodies which specifically bind the immunogenic substance (i.e., a humoral response). An immunogenic substance may in addition elicit a cellular immunological response. Such an immunogen is any of the immunogenic peptides obtained by screening a library of random peptides using monoclonal antibodies that immunospecifically react with PsaA from *S. pneumoniae*.

As used herein, "immune response" and "immunogenic response" may include at least a humoral response, that is, the generation of antibodies which specifically bind the immunogenic substance. An immunogenic response may, either alternatively or in addition, refer to a cellular immunological response.

As used herein, "protective immunity" refers to a state in which a subject has generated antibodies, at least some of which are neutralizing antibodies, in response to exposure to a pathogen-related immunogen. Neutralizing antibodies bind the immunogenic component of the pathogen in such a way that proliferative infection by the pathogen is inhibited or abrogated, such that the subject remains essentially free of symptomatic disease. Protective immunity may also arise from an alternative immunogenic response which leads to inactivation, loss, or destruction of the pathogenic agent.

As used herein, "immunostimulatory carrier" relates to any of a variety of immunogenic biological polymers which themselves elicit immune responses when introduced into a subject. Immunostimulatory carriers, when employed in conjunction with an immunogen of interest, such as the peptides of the present invention, provide enhanced immunogenic response in the subject to the immunogen of interest. Furthermore, as used herein, "adjuvant" relates to a composition that enhances the immunogenic activity of an immunogenic substance when administered in conjunction with that substance.

As used herein, a "library" refers to a set of fragments derived from a biological macromolecule, wherein each member of the set is a candidate for possessing a desired biological activity expressing a desired biological function. A library is either a peptide library or a library of oligonucleotide fragments, each member of which contains a nucleotide sequence which encodes a particular member of the peptide library. In the present invention, the peptide library is a set of peptides which are coded for by a random oligonucleotide library. The desired activity for a given peptide is that the peptide be immunogenic in a subject against S. pneumoniae.

As used herein, a "subject" is a mammal in whom it is desired to elicit an immune response to the pathogenic organism S. pneumoniae. A principal class of subjects of the present invention is human beings, especially infants and elderly people, in whom S. pneumoniae is in fact pathogenic. In human subjects, therefore, the immune response is intended to be a protective immune response. For non-human mammals, S. pneumoniae may or may not be inherently pathogenic. Such non-human subjects employed as experimental animals which provide an immune response can be useful in characterizing and optimizing the compositions and methods of the invention. Such mammals include, by way of non-limiting example, mice, rats, and non-human primates. An additional class of subjects includes animals served in veterinary practice, including pets and livestock animals. If S. pneumoniae is pathogenic in such subjects, eliciting protective immunity is desirable.

"Purified protein" as used herein means that the protein or fragment is sufficiently free of contaminants or cell components with which the protein normally occurs as to distinguish the protein from the contaminants or cell components. It is not contemplated that "purified" necessitates having a preparation that is technically totally pure (homogeneous), but purified as used herein means the protein or polypeptide fragment is sufficiently separated from contaminants or cell components with which it normally occurs to provide the protein in a state where it can be used in an assay, such as immunoprecipitation or ELISA. For example, the purified protein can be in an electrophoretic gel.

As used herein, "stringent conditions" refers to the washing conditions used in a nucleic acid hybridization protocol. In general, the washing conditions should be a combination of temperature and salt concentration chosen so that the denaturation temperature is approximately 5–20° C. below the calculated $T_m$ of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The $T_m$ of such an oligonucleotide can be estimated by allowing about 2° C. for each A or T nucleotide and about 4° C. for each G or C. For example, an 18 nucleotide probe of 50% G-C would, therefore, have an estimated $T_m$ of 54° C.

As used herein, a "therapeutic composition" relates to a composition which may be administered to a subject in order to elicit a protective immune response, and which contains one or more of the immunogenic peptides of the present invention in conjunction with an immunostimulatory carrier or an adjuvant. The therapeutic compositions contain the peptide and the carrier in either a mixture or as a chemical conjugate. Together these constitute the active agent. If more than one peptide is employed and the composition is a conjugate, each peptide is conjugated to an immunostimulatory carrier. In addition, the therapeutic composition generally contains the components of a pharmaceutical formulation in which the active agent is suspended or dissolved. The components of pharmaceutical formulations are-well known to those who are skilled in immunology or pharmaceutical science. The formulation should be suitable to administer the active agent to a subject in order to elicit an immune response and confer protective immunity against the pathogen related to the immunogenic peptide.

As used herein, the term "allelic variation" or "allelic variant" refers to an immunogenic PsaA peptide or protein obtained from a serotype of S. pneumoniae other than that of a reference serotype such as serotype 2. An allelic variant describes the same 37-kDa pneumococcal surface adhesin protein, or a similar protein that is diverged from the 37-kDa Streptococcus pneumoniae protein set forth in the Sequence Listing as SEQ ID NO:2 by less than 15% in its corresponding amino acid identity. Preferably, this allelic variant is less than 10% divergent in its corresponding amino acid identity, more preferably less than 7% divergent, more preferably less than 5% divergent, more preferably less than 3% divergent, more preferably less than 2% divergent, and most preferably less than 1% divergent in their corresponding amino acid identity. These amino acids can be substitutions within the amino acid sequence set forth in the Sequence Listing as SEQ ID NO:2, or the variants can be either deletions from or additions to the amino acid sequence set forth in the Sequence Listing as SEQ ID NO:2.

Nucleic Acids

In one aspect, the invention provides an isolated nucleic acid encoding the 37-kDa protein of Streptococcus pneumoniae whose amino acid sequence is set forth in the Sequence Listing as SEQ ID NO:2. The term "isolated" refers to a nucleic acid which is essentially separated from other genes that naturally occur in S. pneumoniae. In one embodiment, the present invention provides an isolated nucleic acid encoding the 37-kDa protein of Streptococcus pneumoniae wherein the nucleic acid is the nucleic acid whose nucleotide sequence is set forth in the Sequence Listing as SEQ ID NO:1. An isolated nucleic acid comprising a unique fragment of at least 10 nucleotides of the nucleic acid set forth in the Sequence Listing as SEQ ID NO:1 is also provided. "Unique fragments," as used herein, means a nucleic acid of at least 10 nucleotides that is not identical to any other known nucleic acid sequence at the time the invention was made. Examples of the sequences of at least 10 nucleotides that are unique to the nucleic acid set forth in the Sequence Listing as SEQ ID NO:1 can be readily ascertained by comparing the sequence of the nucleic acid in question to sequences catalogued in GenBank, or other sequence database, using computer programs such as DNA-SIS (Hitachi Engineering, Inc.), or Word Search or FASTA of the Genetics Computer Group (GCG) (Madison, Wis.), which search the catalogued nucleotide sequences for similarities to the nucleic acid in question. If the sequence does not match any of the known sequences, it is unique. For example, the sequence of nucleotides 1–10 can be used to search the databases for an identical match. If no matches are found, then nucleotides 1–10 represent a unique fragment. Next, the sequence of nucleotides 2–11 can be used to search the databases, then the sequence of nucleotides 3–12, and so on up to nucleotides 1321 to 1330 of the sequence set forth in the Sequence Listing as SEQ ID NO:1. The same type of search can be performed for sequences of 11 nucleotides, 12 nucleotides, 13 nucleotides, etc. The possible fragments range from 10 nucleotides in length to 1 nucleotide less than the sequence set forth in the Sequence Listing as SEQ ID NO:1. These unique nucleic acids, as well as degenerate nucleic acids can be used, for example, as primers for amplifying nucleic acids from other strains of Streptococcus pneumoniae in order to isolate allelic variants of the 37-kDa protein, or as primers for reverse transcription of 37-kDa protein RNA, or as probes for use in detection techniques such as nucleic acid hybridization. One skilled in the art will appreciate that even though a nucleic acid of at least 10 nucleotides is unique to a specific gene, that nucleic acid fragment can still hybridize to many other nucleic acids and therefore be used in techniques such as amplification and nucleic acid detection.

Also provided are nucleic acids which encode allelic variants of the 37-kDa protein of S. pneumoniae set forth in the Sequence Listing as SEQ ID NO:2. The homology between the protein coding region of the nucleic acid encoding the allelic variant of the 37-kDa protein is preferably less than 20% divergent from the region of the nucleic acid set forth in the Sequence Listing as SEQ ID NO:1 encoding the 37-kDa protein. Preferably, the corresponding nucleic acids are less than 15% divergent in their sequence identity. In another embodiment, the corresponding nucleic acids are less than 10% divergent in their sequence identity, more preferably less than 7% divergent, more preferably less than 5% divergent, more preferably less than 4% divergent, more preferably less than 3% divergent, more preferably less than 2% divergent, and most preferably less than 1% divergent in their corresponding nucleotide identity. In particular, the nucleic acid variations can create up to about 15% amino acid sequence variation from the protein set forth in the Sequence Listing as SEQ ID NO:2.

One skilled in the art will appreciate that nucleic acids encoding homologs or allelic variants of the 37-kDa protein set forth in the Sequence Listing as SEQ ID NO.2 can be isolated from related gram-positive bacteria. The nucleic acid encoding a 37-kDa protein may be obtained by any number of techniques known to one skilled in the art. Methods of isolating nucleic acids of the invention, including probes and primers that may be used, are set forth in U.S. patent application Ser. No. 08/715,131, filed Sep. 17, 1996 (now U.S. Pat. No. 5,854,416), which is a continuation-in-part of U.S. patent application Ser. No. 08/222,179, filed Apr. 4, 1994, which is a continuation-in-part of U.S. patent application Ser. No. 07/791,377, filed Sep. 17, 1991 (now U.S. Pat. No. 5,422,427). General methods that may be employed for these purposes are set forth in Sambrook et al., "Molecular Cloning: a Laboratory Manual," Cold Spring Harbor Laboratory Press (1989), and Ausubel et al. "Current Protocols in Molecular Biology," John Wiley and Sons, New York, 1987 (updated quarterly). Amplification procedures that may be employed in the nucleic acid isolation protocols are well known to those skilled in the art (see, for example, Innis et al., 1990, "PCR Protocols: A Guide to Methods and Applications," Academic Press, Inc. An example of amplification of a nucleic acid encoding the 37-kDa protein of Streptococcus pneumoniae serotype 6B is discussed in the Example contained herein.

37-kDa Protein

The present invention also provides a purified polypeptide as set forth in the Sequence Listing as SEQ ID NO:2 and a purified polypeptide encoded by a nucleic acid comprising a unique fragment of at least 10 nucleotides of SEQ ID NO:1. The protein can be used as a vaccine component as well as a reagent for identifying subject antibodies raised against Streptococcus pneumoniae during infection. The purified protein can also be used in methods for detecting the presence of Streptococcus pneumoniae.

Unique fragments of the 37-kDa protein can be identified in the same manner as that used to identify unique nucleic acids. For example, a sequence of 3 amino acids or more, derived from the sequence of the 37-kDa protein, as set forth in the Sequence Listing as SEQ ID NO:2, can be used to search the protein sequence databases. Those that do not match a known sequence are therefore unique. Methods of preparing these proteins and protein fragments are set forth in U.S. patent application Ser. No. 08/715,131, filed Sep. 17, 1996, (now U.S. Pat. No. 5,854,416) which is a continuation-in-part of U.S. patent application Ser. No. 08/222,179, filed Apr. 4, 1994, which is a continuation-in-part of U.S. patent application Ser. No. 07/791,377, filed Sep. 17, 1991 (now U.S. Pat. No. 5,422,427).

The present invention provides peptide fragments related to the 37-kDa pneumococcal surface adhesin protein. The polypeptide fragments of the present invention can be recombinant polypeptides obtained by cloning nucleic acids encoding fragments of the polypeptide in an expression system capable of producing the polypeptide fragments thereof, as described above for the 37-kDa protein. For example, one can identify an immunoreactive peptide related to the 37-kDa pneumococcal surface adhesin protein which can cause a significant immune response by using antibodies raised against the adhesin protein, cloning the nucleic acid encoding that polypeptide into an expression vector, and isolating that particular polypeptide for further uses, such as diagnostics, therapy, and vaccination. Amino acids which do not contribute to the immunoreactivity and/or specificity can be deleted without a a loss in the respective activity. For example, amino or carboxy-terminal amino acids can be sequentially removed from any peptide identified using the procedure outlined above, and the immunoreactivity tested in one of many available assays. Alternatively, internal amino acids can be sequentially removed and the immunoreactivity tested for each of the deletions.

In another example, a peptide fragment related to a 37-kDa pneumococcal surface adhesin protein can comprise a modified polypeptide wherein at least one amino acid has been substituted for the amino acid residue originally occupying a specific position, or a portion of either amino terminal or carboxy terminal amino acids, or even an internal region of the polypeptide, can be replaced with a polypeptide fragment or other moiety, such as biotin, which can facilitate in the purification of the modified 37-kDa pneumococcal surface adhesin protein.

Immunoreactive peptide fragments related to a 37-kDa pneumococcal surface adhesin protein can include insertions, deletions, substitutions, or other selected modifications of particular regions or specific amino acid residues, provided the immunoreactivity of the peptide is not significantly impaired compared to the 37-kDa pneumococcal surface adhesin protein. These modifications can provide for some additional property, such as to remove/add amino acids capable of disulfide bonding, to increase its biolongevity, and the like. In any case, the peptide must possess a bioactive property, such as immunoreactivity, comparable to the 37-kDa pneumococcal surface adhesin protein.

Antibodies

The present invention employs a purified antibody which selectively binds with the polypeptide encoded by the nucleic acid set forth in the sequence listing as SEQ ID NO:1, or a polypeptide encoded by a unique fragment of at least 10 nucleotides of SEQ ID NO: 1. The antibody (either polyclonal or monoclonal) can be raised to the 37-kDa pneumococcal surface adhesin protein or a unique fragment thereof, in its naturally occurring form or in its recombinant form. The antibody can be used in a variety of techniques or procedures such as diagnostics, treatment, or immunization. Antibodies can be prepared by many well-known methods (see, e.g., Harlow and Lane, "*Antibodies: A Laboratory Manual*", Cold Spring Harbor Laboratory, Cold Spring Harbor, N.Y., (1988)). Briefly, purified antigen can be injected into an animal in an amount and at intervals sufficient to elicit an immune response. Antibodies can be purified directly, to yield polyclonal antibodies. Alternatively, spleen cells can be obtained from the animal. The cells can be then fused with an immortal cell line and screened for antibody secretion to yield monoclonal antibodies. The antibodies can be used to screen nucleic acid clone libraries for cells secreting the antigen. Those positive clones can then be sequenced (see, e.g., Kelly et al., Bio Technology, 1992, 10:163–167: Bebbington et. al., 1992, *Bio Technology*, 10:169–175).

The phrase "selectively binds" with the polypeptide refers to a binding reaction which is determinative of the presence of the protein in a heterogeneous population of proteins and-other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies which selectively bind with a particular protein. For example, solid-phase ELISA immunoassays are routinely used to select antibodies selectively immunoreactive with a protein. See Harlow and Lane, "*Antibodies: A Laboratory Manual*," Cold Spring Harbor Publications, New York, (1988), for a description of immunoassay formats and conditions that could be used to determine selective binding. In some instances, it is desirable to prepare monoclonal antibodies from various subjects. A description of techniques for preparing such monoclonal antibodies may be found in Stites et al., editors, "*Basic and Clinical Immunology*," (Lange Medical Publications, Los Altos, Calif., Fourth Edition) and references cited therein, and in Harlow and Lane ("*Antibodies: A Laboratory Manual*," Cold Spring Harbor Publications, New York, (1988)).

The monoclonal antibodies (MAbs) employed in the present invention (disclosed in U.S. patent application Ser. No. 08/715,131, filed Sep. 17, 1996 (now U.S. Pat. No. 5,854,416), incorporated herein by reference) are MAb 1 E7A3D7C2, or a fragment thereof which retains the characteristics of antibody 1 E7A3D7C2, such as its binding specificity and its binding affinity; MAb 1 B6E12H9, or a fragment thereof which retains the characteristics of antibody 1 B6E12H9; MAb 3C4D5C7, or a fragment thereof which retains the characteristics of antibody 3C4D5C7; MAb 4E9G9D3, or a fragment thereof which retains the characteristics of antibody 4E9G9D3; MAb 4H5C10F3, or a fragment thereof which retains the characteristics of antibody 4H5C10F3; MAb 6F6F9C8, or a fragment thereof which retains the characteristics of antibody 6F6F9C8; and MAb 8G12G11 B10, or a fragment thereof which retains the characteristics of antibody 8G12G11B10.

The hybridomas used to produce the respective monoclonal antibodies employed in the present invention (disclosed in U.S. patent application Ser. No. 08/715,131, filed September 17, 1996 (now U.S. Pat. No. 5,854,416), incorporated herein by reference) are hybridoma 1 E7A3D7C2, hybridoma 1B6E12H9, hybridoma 3C4D5C7, hybridoma 4E9G9D3, hybridoma 4H5C10F3, hybridoma 6F6F9C8, and hybridoma 8G12G11B10.

Therapeutic Compositions

Also provided by the present invention is a therapeutic composition comprising an immunogenic polypeptide encoded by the nucleic acid as set forth in the Sequence Listing as SEQ ID NO:1, or a unique fragment of at least 10 nucleotides of SEQ ID NO:1. The invention also provides therapeutic compositions comprising at least one immunogenic polypeptide that immunospecifically binds to a monoclonal antibody obtained in response to immunizing an animal with *Streptococcus pneumoniae* PsaA. The therapeutic composition is preferably combined with an immunostimulatory carrier. The therapeutic composition confers protective immunity against *S. pneumoniae* infection when administered to a subject.

The polypeptides provided by the present invention can be used to vaccinate a subject for protection from a particular disease, infection, or condition caused by the organism from which the 37-kDa pneumococcal surface adhesin protein (or a unique fragment thereof) was derived. Polypeptides of a 37-kDa pneumococcal surface adhesin protein of serotype 6B, or a unique fragment thereof, can be used to inoculate a subject organism such that the subject generates an active immune response to the presence of the polypeptide or polypeptide fragment which can later protect the subject from infection by organism from which the polypeptide was derived. One skilled in the art will appreciate that an immune response, especially a cell-mediated immune response, to a 37-kDa pneumococcal surface adhesin protein from a specific strain can provide later protection from reinfection or from infection from a closely related strain. The 37-kDa protein provided by the present invention, however, is relatively conserved among the 90 serotypes of *S. pneumoniae* and can, therefore, serve as a multivalent vaccine. Immunization with the 37-kDa pneumococcal surface adhesin protein or with the immunogenic peptides of the invention can be achieved by administering to subjects the 37-kDa pneumococcal surface adhesin protein either alone or with a pharmaceutically acceptable carrier, (Kuby, J. 1992 *"Immunology,"* W. H. Freeman and Co., New York). Immunogenic amounts of the 37-kDa pneumococcal surface adhesin protein or of the immunogenic peptides of the invention can be determined using standard procedures. Briefly, various concentrations of the present polypeptide are prepared, administered to subjects, and the immunogenic response (e.g., the production of antibodies to the polypeptide or cell mediated immunity) to each concentration is determined. Techniques for monitoring the immunogenic response, both cellular and humoral, of patients after inoculation with the polypeptide, are well known in the art. For example, samples can be assayed using enzyme-linked immunosorbent assays (ELISA) to detect the presence of specific antibodies, such as serum IgG (Hjelt et al., *J. Med. Virol.,* 21:39–47, (1987)); lymphocyte or cytokine production can also be monitored. The specificity of a putative immunogenic antigen of any particular polypeptide can be ascertained by testing sera, other fluids, or lymphocytes from the inoculated patient for cross-reactivity with other closely related 37-kDa pneumococcal surface adhesin proteins. The amount of a polypeptide of the 37-kDa pneumococcal surface adhesin protein or of the immunogenic peptides of the invention to be administered will depend on the subject, the condition of the subject, the size of the subject, and the like, but will be at least an immunogenic amount. The polypeptide can be formulated with adjuvants and with additional compounds, including cytokines, with a pharmaceutically acceptable carrier.

The pharmaceutically acceptable carrier or adjuvant in the therapeutic composition of the present invention can be selected by standard criteria (Arnon, R. (Ed.) *"Synthetic Vaccines,"* 1:83–92, CRC Press, Inc., Boca Raton, Fla., 1987). By "pharmaceutically acceptable" is meant a material that is not biologically or otherwise undesirable (i.e., the material may be administered to an individual along with the selected compound without causing any undesirable biological effects or interacting in an undesirable manner with any of the other components of the pharmaceutical composition in which it is contained). The carrier or adjuvant may depend on the method of administration and the particular patient. Methods of administration can be parenteral, oral, sublingual, mucosal, inhaled, absorbed, or injection. Actual methods of preparing the appropriate dosage forms are known, or will be apparent, to those skilled in this art: see, for example, Remington's *Pharmaceutical Sciences* (Martin, E. W. (ed.) latest edition Mack Publishing Co., Easton, Pa.). Parenteral administration, if used, is generally characterized by injection. Injectables can be prepared in conventional forms, either as liquid solutions or suspensions, solid forms suitable for solution or suspension in liquid prior to injection, or as emulsions. Another approach for parenteral administration involves use of a slow release or sustained release system, such that a constant level of dosage is maintained (see, e.g., U.S. Pat. No. 3,710,795). In addition, powders or aerosols may be formulated for administration by inhalation.

Detection Methods

The present invention provides methods of detecting the presence of *Streptococcus pneumoniae* in a subject, based on several variations of immunoassays, using either a purified polypeptide encoded by the nucleic acid set forth in the Sequence Listing as SEQ ID NO:1, a purified polypeptide encoded by a nucleic acid comprising a unique fragment of at least 10 nucleotides of SEQ ID NO:1, an antibody which selectively binds the purified polypeptide encoded by the nucleic acid set forth in the Sequence Listing as SEQ ID NO: 1, or an antibody which selectively binds a purified polypeptide encoded by a nucleic acid comprising a unique fragment of at least 10 nucleotides of SEQ ID NO:1, and detecting the binding of the antibody with the polypeptide, the binding indicating the presence of *Streptococcus pneumoniae* in the subject. There are numerous immunodiagnostic methods that can be used to detect antigen or antibody as the following non-inclusive examples illustrate. These methods, as well as others, can not only detect the presence of antigen or antibody, but quantitate antigen or antibody as well. These methods are set forth in U.S. patent application Ser. No. 08/715,131, filed Sep. 17, 1996 (now U.S. Pat. No. 5,854, 416), which is a continuation-in-part of U.S. patent application Ser. No. 08/222,179, filed Apr. 4, 1994, which is a continuation-in-part of U.S. patent application Ser. No. 07/791,377, filed Sep. 17, 1991 (now U.S. Pat. No. 5,422, 427). In general, the detection methods that may be employed in practicing the present invention are described in, for example, Harlow et al., *"Antibodies: A Laboratory Manual,"* Cold Spring Harbor Laboratory, Cold Spring Harbor, N.Y., (1988).

Methods of Treating and Preventing Infection

The present invention also provides a method of preventing *Streptococcus pneumoniae* infection in a subject at risk of infection by *S. pneumoniae,* comprising administering to the subject an effective amount of a therapeutic composition comprising an immunogenic polypeptide encoded by the nucleic acid encoding the 37-kDa protein of *Streptococcus pneumoniae* as set forth in the Sequence Listing as SEQ ID NO:1, or an immunogenic polypeptide encoded by a nucleic acid comprising a unique fragment of at least 10 nucleotides of SEQ ID NO:1, or the immunogenic peptides of the invention either alone or with a pharmaceutically acceptable carrier.

The present invention further provides a method of treating a *Streptococcus pneumoniae* infection in a subject, comprising administering to the subject an effective amount of an antibody to the polypeptide encoded by the nucleic acid asset forth in the Sequence Listing as SEQ ID NO:1, or a polypeptide encoded by a nucleic acid comprising a unique fragment of at least 10 nucleotides of SEQ ID NO:1, either alone or with a pharmaceutically acceptable carrier. Treating a subject already infected with a particular organism by administering to the subject an antibody against the organism is well known in the art. For example, immune globulin isolated from animals or humans previously exposed to rabies virus is currently a therapy for rabies virus infection. Better treatment of infected individuals can be achieved by administering to those individuals monoclonal antibodies since those monoclonals react or bind more specifically than the polyclonals, (see, e.g., Kaplan et al., "Rabies," *Sci. Am.* 242:120–134 (1980)).

Epitopic Immunogenic Peptides

The present invention discloses novel epitopic immunogenic peptides obtained as the peptides coded in a random oligonucleotide library by selecting for high affinity binding of the epitopes to monoclonal antibodies specific for epitopes on the PsaA antigen.

In an additional method, a procedure known as "biopanning" or "panning", a target protein or peptide is selected from a library expressed as a heterologous insert on an external surface of a microorganism. A bacterium or virus, for example, may have a nucleotide sequence encoding a heterologous peptide or protein sequence incorporated into its chromosomal nucleic acid in such a way that a fusion or chimera is created. The fusion represents a natural protein of the microorganism directly linked with the heterologous peptide or protein. Once expressed on the surface of the microorganism, it can be probed by a ligand specific for the sought peptide or protein, such as an antibody. Once identified by capture, the heterologous sequence, either the nucleic acid or the protein, can be obtained and identified.

A common implementation of this procedure is well known to those of skill in the fields of protein chemistry, immunology, and virology. A filamentous bacteriophage such as M13, fl, or fd is employed. These bacteriophages have two well-known structural proteins on their surfaces: the gene III protein and the gene VIII protein. The nucleic acid of the phage is altered by incorporating a fusion sequence of the heterologous peptide in frame with the gene for one or the other of these structural proteins. When one is seeking a target peptide from among a large set, or library, of such peptides, the corresponding library of heterologous nucleotide sequences coding for the members of the peptide library is incorporated into the structural protein gene. The resulting bacteriophage population (termed a phage display library) is subjected to procedures which optimize selection of only those virus particles expressing members of the peptide library for which the PsaA-specific ligand, such as an MAb, has a high affinity. The bacteriophage particles so selected may then be amplified by further culture, or their nucleic acids may be amplified by methods such as polymerase chain reaction. In this way the nucleic acid of the captured particle may be isolated and sequenced to provide the coding sequence for the high affinity epitope bound to the MAb or other ligand. Biopanning is described for example, in Smith, G. P. and K. K. Scott (1993, "Libraries of Peptides and Proteins Displayed on Filamentous Phage", *Meth. Enzymol.* 217: 228–257).

The immunogenic peptides of the invention were obtained using a biopanning procedure that has general applicability for identifying the sequence of a peptide potentially capable of eliciting protective immunity against a pathogenic microorganism. The method includes the steps of (a) providing a library comprised of random oligonucleotides, wherein the oligonucleotides are about 30–45 nucleotides in length;

(b) splicing the oligonucleotides of a library into the gene for a coat protein of a filamentous bacteriophage in frame with the codons for the amino acid residues of the coat protein, such that the gene for the coat protein is contained within the complete nucleic acid that is the genome for the bacteriophage, thereby creating a bacteriophage library, and further positioning the oligonucleotides within the gene such that when the coat protein is expressed and incorporated into a complete bacteriophage particle the peptide is available, by exposure on the surface, as an epitope to which an antibody can bind;

(c) expanding the bacteriophage library harboring the oligonucleotide library by culturing the bacteriophage library in a host which the bacteriophage infects;

(d) screening the expanded bacteriophage library for any bacteriophage particle that immunospecifically reacts with a monoclonal antibody obtained in response to immunizing an animal with an immunogen of the microorganism; and (e) sequencing the gene for the coat protein of any bacteriophage particle obtained in step (d) thereby yielding the nucleotide sequence of that member of the oligonucleotide library whose translation product has the sequence of a peptide potentially capable of eliciting protective immunity against *Streptococcus pneumoniae*.

In the particular application employed in obtaining the immunogenic peptides of the invention, the method described above is directed against *S. pneumoniae*, the coat protein is the gene III protein which is the tail protein of a filamentous bacteriophage such as M13, fl, or fd, and the monoclonal antibody is obtained in response to immunizing an animal with *Streptococcus pneumoniae* pneumococcal surface adhesion A protein (PsaA). The peptides are isolated using a procedure that emphasizes capturing only those peptides that have a high affinity for the antibodies. This assures that any protective effect based on humoral immunity will be highly effective.

The sequences of the peptides which bind to the antibodies may be identified by sequencing the gene III fusion of the bacteriophage particle obtained in the biopanning process. The actual immunogenic peptides may then be synthesized in conventional peptide synthesizers. These peptides are then incorporated into a therapeutic composition in which the immunogenic peptides are combined with an immunostimulatory carrier to be administered to a subject. Upon being administered in effective amounts, the subject elicits the production of antibodies against *S. pneumoniae*. This results in conferring protective immunity against infection by *S. pneumoniae* on the subject.

PsaA is a 37-kDa species-common protein from *S. pneumoniae* (*pneumococcus*) which is effectively immunogenic. It is common to all the serotypes whose polysaccharides are components of the pneumococcal vaccine currently in use (Russell et al., 1990, "Monoclonal antibody recognizing a species-specific protein from *Streptococcus pneumoniae*", J. Clin. Microbiol. 28:2191–2195). The sequence of the PsaA gene cloned from serotype R36A has been described (U.S. Pat. No. 5,422,427 to Russell et al.), and the sequence of PsaA protein was deduced. In addition, the nucleotide sequence of cloned PsaA from serotypes 2 and 6B, and their corresponding amino acid sequences, have been determined (Berry et al., 1996, "Sequence heterogeneity of PsaA, a 37-kilodalton putative adhesin essential for virulence of *Streptococcus pneumoniae*", Infect. Immun. 64: 5255–5262; Sampson et al., 1997, "Limited Diversity of *Streptococcus pneumoniae* PsaA among Pneumococcal Vaccine Serotypes", *Infect Immun.* 65 1967–1971). Excluding the putative leader sequence, there are 6 amino acid differences between PsaA's from serotype 6B versus serotype 2, out of a total of 290 residues overall; there are 45 amino acid differences between 6B and 36A (Sampson et al., ibid). This result led Sampson et al. to suggest that serotypes 2 and 6B represent the prototypical sequences among pneumococcal PsaA proteins. PsaA from serotype 3 (disclosed in U.S. patent application Ser. No. 08/715,131 now U.S. Pat. No. 5,854,416, incorporated herein by reference) and serotype 22 (Talkington et al., 1996, "Protection of mice against fatal pneumococcal challenge by immunization with pneumococcal surface adhesin A (PsaA)", *Microb. Pathhog.* 21:17–22) effectively provide protective immunity in mice against challenge doses of *S. pneumoniae*.

The peptides of the present invention contain immunogenic epitopes selected by binding to PsaA-specific monoclonal antibodies. Preferably the peptide is about 10–25 residues in length. More preferably, the peptide is about 12–22 residues in length, and most preferably about 15 residues in length. In the embodiments presented in the Examples below, the peptides are given in SEQ ID NO:5, SEQ ID NO:6, SEQ ID NO:7, and SEQ ID NO:8. In addition, the invention encompasses immunogenic peptides which may be shorter than these sequences. Thus, for example, immunogenic fragments of SEQ ID NO:5, immunogenic fragments of SEQ ID NO:6, immunogenic fragments of SEQ ID NO:7, and immunogenic fragments of SEQ ID NO:8 are also encompassed by the present invention.

Currently approximately 90 serotypes of S. pneumoniae have been identified; these may have PsaA antigens which are allelic variants of the PsaA sequences already identified. The invention therefore encompasses an allelic immunogenic peptide which, for example, was obtained by a biopanning procedure in which the monoclonal antibodies were raised by immunizing with an allelic variant, or in other ways known to those skilled in the relevant arts. The sequence of such a peptide is at least 80% identical to any of the following sequences: SEQ ID NO:5, SEQ ID NO:6, SEQ ID NO:7, SEQ ID NO:8, immunogenic fragments of SEQ ID NO:5, immunogenic fragments of SEQ ID NO:6, immunogenic fragments of SEQ ID NO:7, and immunogenic fragments of SEQ ID NO:8.

The monoclonal antibodies (MAbs) disclosed above were used further in procedures of the present invention. The specific MAbs that were used are designated 1E7 (1E7A3D7C2), 6F6 (6F6F9C8), 4E9 (4E9G9D3), 8G12 (8G12G11B1O), and 1B6 (1B6E12H9). These MAbs were obtained as a result of immunization of an animal with PsaA; such antibodies therefore represent molecules whose antigen-binding domains bind immunogenic epitopes of the invention.

Identification of immunogenic epitopes related to PsaA may be achieved in any of a number of ways. Methods to identify immunogenic epitopes may employ any MAb obtained in response to primary immunization with PsaA. Any procedure which narrows down the overall molecular structure of PsaA to moieties or fragments thereof may be employed in identifying immunogenic epitopes thereof. In one method, chemical modification of specific residues of PsaA yields modified products whose reactivity with a ligand such as an anti-PsaA MAb may be impaired. Knowledge of which residue or residues were modified in products with impaired binding may be used to identify those residues as potentially being a portion of the epitope. Additionally, biopanning, described above, may be used.

In another method, fragments of PsaA may be synthesized chemically by peptide synthesis. In general, a set of peptides are synthesized which represents a systematic progression along the entire sequence of the protein from its N-terminus to its C-terminus. Windows of predetermined lengths may be "walked" along the protein sequence generating a set of peptides which encompasses most or all of the original sequence. Methods of peptide synthesis are well-known to workers of skill in the fields of peptide chemistry, protein chemistry, and immunology. Commercial instruments are available for the automated synthesis of peptides once their sequences are specified. A set of peptides obtained in this way may be subjected to assays which establish whether they bind to PsaA-specific ligands, such as anti-PsaA MAbs. Immunoassay methods are preferred for such determinations and are well-known to workers of skill in immunology. They include procedures such as enzyme-linked immunosorbent assays (ELISA), using, for example, competitive formats or direct heterogeneous formats. Peptides found to bind with high affinity to the PsaA-specific ligands are presumed to contain or encompass an immunogenic epitope of PsaA.

The immunogenic peptides of the invention are identified in the selection or screening procedures described in the preceding paragraphs. The sequences of the peptides positively selected next need to be obtained. In the case of chemical modification, the location of inhibitory modifications in the sequence yields peptides centered on, or containing, that modified residue. In the case of the screening of synthesized peptides, the sequence is immediately available from the identity of the positive sample. In the case of biopanning, the positive bacteriophages are isolated and the nucleic acid is amplified, either by expansion of the phage particles in culture or by amplification of the nucleic acid itself. The nucleic acid is then isolated and sequenced to identify the coding sequence for the heterologous peptide and the coding sequence translated to yield the peptide sequence.

Once the sequences are known, the corresponding peptides are synthesized in order to serve as immunogenic peptides in a subject. Methods for synthesizing peptides are well-known to skilled workers in the art of immunochemistry, immunology, and/or protein chemistry. For example, peptides can be synthesized using solid phase F-moc chemistry according to the method of Stewart et al., "Solid peptide synthesis," $2^{nd}$ ed., Pierce Chemical Co., Rockford, Ill. (1984). Typically, such synthesis is carried out on automated peptide synthesizers, such as automated synthesizers available from Advanced ChemTech (Advanced ChemTech, Inc., Louisville, Ky.). An example of a synthesizer that can be used for synthesizing peptides according to the current invention is the Advanced ChemTech ACT model 396 MPS. Once synthesized, sequences are typically verified using an automated peptide sequencer such as a Porton model 2090 (Beckman Instruments Inc., Mountain View, Calif.).

As is demonstrated in the Examples below and discussed in the "37-kDa Protein" section above, peptides of the current invention can include insertions, deletions, substitutions, or other selected modifications of particular regions or specific amino acid residues provided the immunoreactivity of the peptide is not significantly impaired compared to the 37-kDa pneumococcal surface adhesin protein. The phrase "consisting essentially of" with respect to peptides of the current invention is intended to cover such modified peptides which, as illustrated in the Examples section below, can be identified and routinely generated by those of skill in the art.

In some embodiments, peptides of the current invention are combined with an immunostimulatory carrier and/or with an adjuvant prior to administration to a subject, as is well-known to those of skill in the art of immunochemistry or immunology and discussed herein in the "Therapeutic Compositions" section. In common practice, immunostimulatory carriers are proteins such as keyhole limpet hemocyanin, bovine serum albumin, thyroglobulin, diphtheria toxoid, and the like. The immunogenic peptides and the carrier may be combined either noncovalently or covalently. When combined noncovalently, they are mixed together so that they comprise components in a therapeutic composition to be administered to a subject.

Many adjuvants are known in the art that could be used to stimulate an immune response to peptides of the current invention. For example, alum, proteosomes, certain lipids, such as palmitic acid (see below), QS21, or ALHYDROGEL® (2%; #A1090BS, Accurate Chemical and Scientific Company, Westbury, N.Y.) could be used as an adjuvant in the present invention (da Fonseca, D. P., et al., "Identification of new cytotoxic T-cell epitopes on the 38-kilodalton lipoglycoprotein of *Mycobacterium tuberculosis* by using lipopeptides," *Infect. Immun.* 66:3190 (1998); Sheikh, N. A., et al., "Generation of antigen specific CD8+ cytotoxic T cells following immunization with soluble protein formulated with novel glycoside adjuvants," *Vaccine* 17:2974 (1999); and Moore, A., et al., "The adjuvant combination monophosphoryl lipid A and QS21 switches T cell responses induced with a soluble recombinant HIV protein from Th2 to Th1," *Vaccine* 17: 2517 (1999).

In addition to the conjugates and adjuvants described above, immunogenicity of peptides of the current invention can be enhanced by attachment of the peptides to proteosomes or by addition of a cystein residue. For attachment to proteosomes, a spacer, such as a CYGG (SEQ ID NO: 11) spacer, and a lauroyl group can be attached to the peptide's amino terminal end (Bio-Synthesis, Lewisville, Tex.). The lauroyl group enhances the hydrophobic complexing of peptide groups to proteosomes (Lowell, G. H., et al., "Proteosomes, hydrophobic anchors, iscoms, and liposomes for improved presentation of peptide and protein vaccines," in: *New Generation Vaccines*, Woodrow, G. M., Levine, M. M. (Ed.), Marcel Dekker, Inc., New York, pp. 141–160 (1990); Lowell, G. H., et al., "Peptides bound to proteosomes via hydrophobic feet become highly immunogenic without adjuvants," *J. Exp. Med.* 167:658 (1988); and Zollinger, W. D., et al., "Complex of meningococcal group B polysaccharide and type 2 outer membrane protein immunogens in man," *J. Clin. Invest.* 63:836 (1979)). A cysteine group on the other hand, such as the cysteine in the CYGG spacer described above, enhances the immunogenicity of the peptide (Lowell, G. H., et al., (1990)). Proteosomes can be prepared from the outer membrane complex vesicles from Group B meningococci, strain 99M as described by Zollinger (Zollinger, et al., (1990)). Synthetic lipopeptides can be complexed to proteosomes on a 1:1 (w/w) ratio by combining the components in the presence of detergent. The detergent can be removed by extensive dialysis (Lowell, G. H., et al., (1988)).

In some embodiments, peptides of the current invention are lipidated with, for example, but not limited to, monopalmitic acid, to stimulate an immune response to the peptide (Verhaul et al., "Monopalmitic acid-peptide conjugates induce cytotoxic T cell responses against malarial epitopes: importance of spacer amino acids," *J. Immunol. Methods*, 182:219 (1995)). Lipidated versions of the peptides of the current invention containing monopalmitic acid can be synthesized by coupling palmitic acid (Sigma Chemicals, St. Louis, Mo.) to the deprotected amino-terminus of a resin-bound peptide employing the same reaction conditions as for the standard amino acid couplings described above (Verhaul et al. (1995)). In some embodiments, the tripeptide cysteine-serine-serine is added to the amino terminus of the peptides of the current invention to facilitate attachment of a lipid such as monopalmitic acid.

In addition to attachment of lipids to in vitro synthesized peptides of the current invention, lipidated versions of the peptides of the current invention can be produced using recombinant DNA technology using methods known in the art. For example, constructs can be developed that contain a heterologous leader sequence joined to nucleic acids encoding the peptides of the current invention. The heterologous leader sequence is lipidated by a host organism. The leader sequence may, for example, be derived from the ospA gene of *Borrelia burgdorferi*. (Ades et al., "Recombinant lipidated PsaA protein, methods of preparation and use," PCT Publication WO 99/40200 (1999)).

Therapeutic compositions of the present invention are described in the "Therapeutics Compositions" section above. In preparing therapeutic compositions of the invention, immunogenic peptides are formulated with a pharmaceutically acceptable vehicle for administration to a subject. Such vehicles are well known to those of skill in the pharmaceutical sciences, and include preparations in liquid, gel, or solid forms for administration by oral, sublingual, or parenteral routes, including, but not limited to, intravenous, subcutaneous, intramuscular, mucosal, and inhalation. These dosage forms may be conventional preparations such as solutions or suspensions having immediate bioavailability, or they may be controlled release formulations or devices having the property of releasing the active immunogenic peptide slowly over an extended time period. In preferred embodiments, therapeutic compositions comprising peptides of the present invention confer protective immunity against *S. pneumoniae* in subjects, preferably human subjects, to whom they are administered.

In addition to peptides discovered by the methods herein described, immunogenic fragments of such peptides are also encompassed within the present invention. An immunogenic fragment is any peptide shorter than the peptide from which it is derived (the parent) whose sequence is identical to the sequence of a portion of the parent peptide and which retains immunogenicity. It is generally understood in the field of immunochemistry that such peptides must be at least about six residues long in order to be antigenic. Thus any fragment should be at least six residues in length and may have a maximum length one residue less than the parent peptide. Identifying immunogenic fragments can be accomplished using any method which will identify immunogenicity. These methods include, for example, the biopanning procedure described above, as well as direct demonstration of immunogenicity by combining the candidate peptide with an immunostimulatory carrier to form the active component of a pharmaceutical composition, administering the pharmaceutical composition to a subject and assessing whether an immunogenic response has occurred.

A peptide fragment which has been positively identified as being immunogenic may also be assessed for its ability to elicit protective immunity in a subject. This is carried out using methods described herein for determining whether an experimental subject animal exhibiting an immunogenic response to a PsaA peptide fragment resists a challenge by *S. pneumoniae*.

In some embodiments, peptides of the current invention are administered in conjunction with one another to enhance the effectiveness of the immunization. Administration "in conjunction with" encompasses simultaneous and sequential administration, as well as administration in combined form or separately. For example, in addition to therapeutic compositions in which the active agent is a single immunogenic peptide of the invention, the compositions may include multiple peptides having the sequences given by SEQ ID NO:5, or an immunogenic fragment thereof, SEQ ID NO:6, or an immunogenic fragment thereof, SEQ ID NO:7, or an immunogenic fragment thereof, SEQ ID NO:8, or an immunogenic fragment thereof, SEQ ID NO:9, or an immunogenic fragment thereof, SEQ ID NO:10, or an immunogenic fragment thereof, or a fragment of SEQ ID NO:2 whose length is 10–25 residues, preferably 12–22 residues, or more preferably about 15 residues. In one embodiment, the compositions include peptides having the sequence given by SEQ ID NO:5 and peptides having the sequence given by SEQ ID NO:6. In another embodiment, the compositions include peptides having the sequence given by SEQ ID NO:5 and SEQ ID NO:9.

Multiple Antigenic Peptides

In another embodiment for administering the peptides of the current invention, the peptides are administered as multiple antigenic peptides (MAPS) (FIG. 1). Methods for synthesizing and administering multiple antigenic peptides are known in the art (see, e.g., Reynolds et al., "T and B epitope determination and analysis of multiple antigen peptides for the *Schistosoma mansoni* experimental vaccine triose-phosphate isomerase," *J. Immunol.*, 152: 193 (1994); Basak et al., "Application of the multiple antigenic peptides (MAP) strategy to the production of prohormone convertases antibodies: synthesis, characterization and use of 8-branched immunogenic peptides," *J. Pept. Sci.*, 1: 385 (1995)). In a preferred method, multiple antigenic peptides are synthesized by branching two peptides from lysine residues according to the methods of Tam, J. P., "Multiple antigenic peptide system: A novel design for synthetic peptide vaccines and immunoassay. In *Synthetic Peptides: Approaches to Biological Problems*, J. P. Tam and E. T. Kaiser, eds., Alan R. Liss, Inc., New York, 3–18 (1989).

In one preferred embodiment, MAPS of the current invention comprise at least 2, more preferably at least 3, and most preferably at least 4 copies of one of the peptide of the current invention. Homogeneous MAPS are MAPS which contain the same peptide on each of its arms. Heterogeneous MAPS are MAPS which contain different peptides on its arms. In one embodiment, the homogeneous four-arm MAPS comprise SEQ ID NO:5. In another embodiment the homogeneous four-arm MAPS comprise SEQ ID NO:6. In another embodiment the homogeneous four-arm MAPS comprise SEQ ID NO:7. In another embodiment the homogeneous four-arm MAPS comprise SEQ ID NO:8. In another embodiment the homogeneous four-arm MAPS comprise SEQ ID NO:9. In another embodiment the homogeneous four-arm MAPS comprise SEQ ID NO:10. In another embodiment, MAPS of the current invention are three-arm MAPS having as arm sequences any of the peptides of the current invention, including peptides having the sequences given by SEQ ID NO:5, or an immunogenic fragment thereof, SEQ ID NO:6, or an immunogenic fragment thereof, SEQ ID NO:7, or an immunogenic fragment thereof, SEQ ID NO:8, or an immunogenic fragment thereof, SEQ ID NO:9, or an immunogenic fragment thereof, SEQ ID NO:10, or an immunogenic fragment thereof, or a fragment of SEQ ID NO:2 whose length is 10–25 residues, preferably 12–22 residues, or more preferably about 15 residues. In one embodiment, a first arm of the three-arm MAP comprises a peptide has the sequence given by SEQ ID NO:5, a second arm of the three-arm MAP has the sequence given by SEQ ID NO:9, a third arm of the three-arm MAP has the sequence given by SEQ ID NO:10.

As described above in the "Therapeutic Compositions" section immunogenic amounts of the peptides of the current invention can be determined using standard procedures. For example, initial immunizations may contain between about 1 μg and 10 mg, preferably between about 10 μg and 1 mg, and more preferably between about 50 μg and 500 μg of the peptides of the current invention. Booster immunizations are typically given to the animal receiving the initial immunization. The general timing requirements of booster administrations are known in the art. In one embodiment, booster administrations are given at 3 and 6 weeks after the initial administration. Booster administrations typically contain about one-half of the amount of peptide as the initial immunizations.

Standard techniques may be used for monitoring the immunologic response to the immunizations, as described in the "Therapeutic Compositions" section above. For example, immunological response may be determined using a nasopharyngeal (NP) challenge, as demonstrated in the Examples section below. For NP challenge, a subject or animal, for example a mouse, may be challenged intranasally (IN) with $10^8$ cfu of *Streptococcus pneumonia* suspended in 0.85% physiological saline. After sufficient time for bacterial multiplication, (e.g., 5 days after intranasal challenge), animals are sacrificed and nasal washes are performed and cultured by the method of Wu, H. Y., et al., ("Establishment of a *Streptococcus pneumoniae* nasopharyngeal colonization model in adult mice," *Microb. Pathog.* 23:127 (1997)). The wash can be diluted 3×out to a final dilution of 1:486. Fifty microliters of each dilution can be cultured on blood agar+gentamicin plates (Trypicase soy agar supplemented with 5% defibrinated sheep blood and 0.5% gentamicin). Data from NP colonization and carriage in immunized mice and placebo (PBS)-immunized controls can be analyzed using standard statistical tests such as the t-test or the Mann-Whitney rank sum test. Nasopharyngeal carriage is the number of colony forming units per nose. Nasopharyngeal colonization is either positive or negative for a mouse depending on whether at least 1 cfu forms in 25 μl of nasal wash.

The following examples are put forth so as to provide those of ordinary skill in the art with a complete disclosure and description of the present invention: They are intended to be purely exemplary of the invention and not to limit the scope of what the inventors regard as their invention. Unless indicated otherwise, parts are parts by weight, temperature is in ° C., and pressure is at or near atmospheric.

EXAMPLES

Bacterial strains. The *S. pneumoniae* strain R36A was kindly provided by D E. Briles (University of Alabama at Birmingham). Twenty-four serotypes of *S. pneumoniae* were provided by K. Facklam, Centers for Disease Control (CDC), Atlanta, Ga. These serotypes are 1, 2, 3, 4, 5, 6A, 6B, 7F, 8, 9N, 9V, 10A, 11A, 11F, 12F, 14, 15B, 18C, 19A, 19F, 20, 22F, 23F, and 33F. *Enterococcus avium, E. casscliflavus*, and *E. gallinarum* were also provided by R. Facklam. Anaerobic bacteria were obtained from V. R. Dowell, CDC. These included *Bacteroides asaccharolyticus, B. fragilis, B. intermedius, B. thetaiotaomicron, Eubacterium lentum, Fusobacterium necrophorum, F. nucleatum, Peptostreptococcus anaerobius, P. asaccharolyticus, Propionibacterium acnes*, and *Staphylococcus saccharolyticus. Branhamella catarrhalis*, and *Bordetella parapertussis* were obtained from R. Weaver, CDC. *Mycobacterium tuberculosis* was provided by R. C. Good, CDC. R. Barnes, CDC, provided *Chlamydia pneumoniae*. The following remaining bacteria were from the stock collection of the Immunology Laboratory, CDC: *Bordetella pertussis, Enterobacter aerogenes, E. agglomerans, E. cloacae, E. gergoviae, Escherichia coli, Klebsiella pneumoniae, Haemophilus influenzae* (types a–f), *Legionella micdadei, L. pneumophila, Mycoplasma pneumoniae, Pseudomonas aeruginosa, Serratia marcescens, Staphylococcus aureus, Streptococcus agalactiae, S. equisimilis, S. pyogenes*, and group *G streptococci*.

Production of MAbs. Female BALB/c mice were immunized with whole cell suspensions of *S. pneumoniae* R36A, a rough derivative of the capsular type 2 strain D39 (Avery et al. (1944) *J. Exp. Med.* 79:137–157). The mice were immunized by intravenous injection three times and once by intraperitoneal injection. The maximum number of cells injected at any time was about 10'. Fusion was done on day 25 by using standard procedures (Clafin et al. (1978) *Curr Top, Microbiol. Immunol.* 81:107–109). Spleen cells of 4 mice were fused with Sp2/0-Ag14 myeloma cells (Schulman et al. (1978) *Nature* (London) 276:269–270). Culture fluids of the growing hybridomas were tested for antibodies to *S. pneumoniae* whole cells in an ELISA. A clone designated 1 E7A3D7C2 was one of 10 selected for further study.

ELISA. Screening of hybridoma culture supernatants was done by ELISA. U-bottom microtitration plates (Costar, Cambridge, Mass.) were sensitized with 50 µl of *S. pneumoniae* whole cell suspension ($10^9$ cfu/ml) diluted 1:4,000 in 0.1 M carbonate buffer, pH 9.6, and kept for 16 h at 4° C. The plates were washed 5 times with 0.9% NaCl containing 0.05% TWEEN®-20 (NaCl-T). Culture supernatants (50 µl) from the fusion plates were added to 50 µl of a solution containing 2% bovine serum albumin (BSA). 10% normal rabbit serum, 0.3% TWEEN®-20, and 0.02% Merthiolate in phosphate buffered saline (PBS), pH 7.2, (ELISA diluent, Wells et al. (1987) *J. Clin. Microbiol.* 25:516–521) in the plates and were incubated for 30 min at 37° C. The plates were washed 5 times with NaCl-T. Fifty microliters of goat anti-mouse immunoglobulin horseradish peroxidase conjugate in ELISA diluent was added to each well. The plates were incubated for 30 min at 37° C. The plates were washed, and 50 µl of 3,3',5,5'-tetramethylbenzidine (0.1 mg/ml in 0.1 M sodium acetate, 0.1 M citric acid (pH 5.7) with 0.005% hydrogen peroxide) was added to each well and incubated for 30 min at 37° C. The reaction was stopped by adding 1 ml of 4 M $H_2SO_4$ and the optical density was read on a Dynatech ELISA Reader (Dynatech Laboratories, Inc., Alexandria, Va.) at 450 nm. An optical density of greater than 0. 200 was considered positive.

SDS-PAGE and immunoblot analysis. Sodium dodecyl sulfate-polyacrylamide gel electrophoresis (SDS-PAGE) was performed by the method of Tsang et al. ((1983) *Methods Enzymol.*, 92:377–391), using an 8% acrylamide resolving gel. Equal volumes of sample buffer (5% SDS-10% 2-mercaptoethanol-20% glycerol in 0.01 M Tris HCl, pH 8.0) and cell suspension containing 2.4 µg protein per µl were mixed, heated at 100° C. for 5 min, and a 5-µl sample was applied to 1 of 15 wells. If the final protein content of the portion of sample to be tested was <1.2 µg/µl a volume up to 10 µl of sample was applied to achieve a final concentration of 6 µl of protein per well. Protein concentrations were determined by the method of Markwell et al. ((1978), *Anal. Biochem.* 87:206–210), with BSA as the standard. Proteins separated by SDS-PAGE were either silver stained by the method of Morrissey ((1981) *Anal. Biochem.* 117:307–310) or electroblotted onto nitrocellulose (Schleicher & Schuell, Inc., Keene, N.H.). The immunoblot procedure was done according to the method of Tsang et al. (1983) with slight modifications. The blots were given three 5-min washes with PBS, pH 7.2, containing 0.3% TWEEN®-20 and were gently agitated overnight (16 h) at 25° C. The blots were blocked for 1 h with casein-thimerosal buffer (CTB) (Kenna et al. (1985) *J. Immunol Meth.,* 85:409–419). After three rinses with CTB, the blots were exposed to goat anti-mouse immunoglobulin horseradish peroxidase conjugate (Bio-Rad Laboratories, Richmond, Calif.) for 2 h at 25° C. Conjugate dilutions (1:2,000) were made in CTB. The blots were again rinsed three times with CTB and exposed to 3,3'-diaminobenzidine-4-hydrochloride in PBS, pH 7.2 (0.5 mg/ml), with 0.003% $H_2O_2$ for 5 min at 25° C. Reactivity was expressed as a visible colored band on the nitrocellulose paper. Low molecular-mass protein standards (Bio-Rad) were used in PAGE and immunoblotting. Rabbit antisera to the protein standards were used to develop the standards (Carlone(1986) *Anal. Biochem.* 155:89–91). Molecular masses were calculated by the method of Neville et al. ((1974), *Methods Enzymol.* 32:92–102) using appropriate molecular mass standards.

Immunoelectron-microscopy. Pneumococcal cells were washed two times with PBS and fixed in a freshly made mixture of 1% paraformaldehyde-0.1% glutaraldehyde for 20 min at 4° C. The cells were dehydrated in a graded alcohol series and then in a 1:1 mixture of absolute ethanol and LOWICRYL® K4M (Ladd Research Industries, Inc., Burlington, Vt.) for 1 h at 4° C. The cells were pelleted and suspended in a 1:2 mixture of absolute ethanol and LOWICRYL® K4M for 1 h at 4° C. They were again pelleted and suspended in LOWICRYL® K4M (undiluted) for 16 h at 4° C. The cells were transferred to fresh and undiluted LOWICRYL® K4M two times during the next 24-hour period. The LOWICRYL® K4M-treated cells were imbedded in gelatin capsules and placed in a box lined with aluminum foil. The capsules were hardened using a short-wave LV light source (35 cm distance for 72 h at −20° C.). The box was brought to room temperature, and the capsules were allowed to continue hardening for up to 14 days. Samples of the capsule were cut into 100-µm thin sections and picked up on nickel grids. Grids containing the sample were placed on a droplet of ovalbumin solution in PBS containing sodium azide (E. Y. Laboratories, Inc., San Mateo, Calif.) for 5 min The grids (wet) were transferred to a solution of primary MAbs diluted in a solution of BSA reagent (1% BSA in PBS containing 0.1% TRITON X— 100™, TWEEN®-20, and sodium azide) (E. Y. Laboratories) and incubated for 1 h at room temperature or 18 to 48 h at 4° C. in a moist chamber. For antibody binding controls, other grids were wetted with MAbs against *Legionella pneumophila*. The grids were rinsed two times with PBS and incubated on droplets of goat anti-mouse IgG-labeled colloidal cold particles (20 µm)(E. Y. Laboratories) for 1 h at room temperature. The grids were rinsed two times and post-stained with osmium tetroxide, uranyl acetate, and lead citrate. The grids were examined with a Philips 410 transmission electron microscope.

CBA/CaHN/J Mice. X-linked immune deficiency (xid) CBA/N mice as described by Wicker et al., *Curr. Top. Microbiol. Immunol.* 124:86–101 were used to study the protection afforded by the 37-kDa protein.

Example 1

Monoclonal Antibodies

MAbs were produced by the method of Kohler et al. (1975, "Continuous cultures of fused cells secreting antibody of predefined specificity," *Nature* 256:495–497) as modified by the method of Zola et al. (1982, "Techniques for production and characterization of monoclonal hybridoma antibodies," in J. G. Hurrell (ed.), *Monoclonal hybridoma antibodies: techniques and applications*, CRC Press Inc., Boca Raton, Fla., pp 1–57.) The 37-kDa purified PsaA used for immunization of mice was from *S. pneumoniae* serotype 22F, and had been purified according to the method of Tharpe et al. (1996, "Purification and seroreactivity of pneumococcal surface adhesin A (PsaA)," *Clin. Diagn. Lab Immunol.,* 3: 227–229). All the MAbs were produced by immunizing with purified PsaA from serotype 22F except for 1 E7 (1 E7A3D7C2), which was produced by immunizing with a nonencapsulated strain of *S. pneumoniae*, R36A (Russell et al., 1990, "Monoclonal antibody recognizing a species-specific protein from *Streptococcus pneumoniae*," *J. Clin. Microbiol.* 28: 2191–2195). The PsaA was isolated using procedures set forth in Examples 3 and 5 below. BALB/c mice were initially immunized intraperitoneally with purified protein at a final concentration of 180 µg/ml in a 1:1 emulsion with Freund's incomplete adjuvant (Sigma Chemical Co., St. Louis, Mo.) and phosphate buffered saline pH 7.2. One month later, the mice were boosted with 110 µg/ml purified PsaA without adjuvant. The hybridoma fusion was performed using standard procedures (Clafin et al., 1978, "Mouse myeloma-spleen cell hybrids: enhanced hybridization frequencies and rapid screening procedures," *Curr. Top Microbiol. Immunol.* 81:107–109). Spleen cells from two mice were fused with Sp 2/0-Ag14 myeloma cells (Schulman et al., 1978. "A better cell line for making hybridomas secreting specific antibodies," *Nature* 276:269–270). Sera from immunized mice and tissue culture supernatant from hybridized cells were screened for reactivity against PsaA by ELISA using a goat anti-mouse immunoglobulin-horseradish peroxidase conjugate, and by SDS-PAGE combined with Western blotting to standard PsaA, in conventional procedures. Hybridomas yielding positive results in the screen were expanded and used in the identification of the peptides; these were 6F6 (6F6F9C8), 4E9 (4E9G9D3), 8G12 (8G12G11B10), and 1B6 (1B6E12H9). These MAbs, along with 1E7, were used in this investigation.

By means of dot immunoblot and Western blot assays, these MAbs reacted with clinical isolates of *S. pneumoniae* representing the 23 type-specific serotypes present in the licensed pneumococcal polysaccharide vaccine. The Western blots confirmed that the antigen detected had a molecular mass of 37-kDa. In an extended study of 90 serotypes of *S. pneumoniae*, the five MAbs listed in the previous paragraph (but not including 1E7) reacted with 89 of the 90 serotypes (only 1 B6 failed to react with serotype 16F). These listed MAbs failed to react with *E. coli*, respiratory pathogens, or nonpathogens representing 22 genera and 29 species. MAb 1 E7 correspondingly reacted with all pneumococcal strains tested (24 serotypes) to yield a sensitivity of 100%. For specificity, none of 55 different nonpneumococcal strains of bacteria (representing 19 genera and 36 species) reacted, thus yielding a specificity of 100%.

When required for use in the experiments described in Example 11, the MAbs were biotinylated by incubating 1 mg of the protein in 0.1 M NaHCO$_3$, pH 8.4, with 100 µg of N-hydroxysuccinimidyl-biotin ester (initially dissolved in DMSO).

Example 2

Cloning of the Pneumococcal Surface Adhesin A Gene

*Streptococcus pneumoniae* DNA digested with restriction enzyme Sau3 µl was ligated to BamHI digested pUC13 and transformed into *E. coli* TB1. Recombinant clones were identified by colony immunoblot using the 37-kDa monoclonal antibody. The plasmid pSTR3-1 is an example of the pneumococcal surface adhesin A gene cloned into pUC13.

Example 3

Preparation of Purified 37-kDa Protein Antigen

Two methods for preparing the 37-kDa protein are to be used. (1) *Streptococcus pneumoniae* is to be conventionally cultured and the cells harvested. Purified 37-kDa protein antigen (pneumococcal surface adhesin A) is to be isolated from the *Streptococcus pneumoniae* cell mass by extraction with a non-ionic detergent and further purified by ammonium sulfate fractionation and isoelectric focusing. (Tharpe et al., 1996, "Purification and seroreactivity of pneumococcal surface adhesin A (PsaA)." *Clin. Diagn. Lab. Immunol.* 3: 227–229), (2) *E. coli* TB1 strains containing plasmid pSTR3-1 is to be cultured conventionally and the cells harvested. For improved yields, *E. coli* strains, transformed with an expression vector that carries a strong, regulated prokaryotic promoter and which contains the gene coding for the 37-kDa protein, is to be used. Suitable expression vectors are those that contain a bacteriophage APL Promoter (e.g., pKK1773-3), a hybrid trp-lac promoter (e.g., pET-3a) or a bacteriophage T7 promoter. The 37-kDa protein (PsaA) is then to be extracted from the separated cell mass.

Protection Experiments with 37-kDa Protein

Example 4

Twenty CB A/CaHN/J mice carrying the xid mutation (x-linked immunodeficiency) were used in this protection study. They were tested for protection against challenge with a virulent capsulan type 3 *Streptococcus pneumoniae* strain, WU2. Mice were anesthetized with Ketamine/Rompun and bled infraorbitally to obtain pre-immunization sera. 37-kDa protein (pneumococcal surface adhesin A) was emulsified in complete Freund's adjuvant (CFA) to a protein concentration of 54 µg per ml. Ten mice were injected subcutaneously into 2 axillary and 2 inguinal sites at 0.1 ml per site, delivering approximately 22 µg protein/mouse. Ten control mice were treated identically with CFA and buffer substituting for protein. Fourteen days later, the ten test mice were injected intraperitoneally (IP) with 100 µg of the 37-kDa protein; controls were injected IP with buffer. Eight days following the IP immunizations, all mice were bled infraorbitally to obtain post-immunization sera, and challenged intravenously (IV) with 60 cfu of a log phase culture of *S. pneumoniae* strain WU2. Mice were observed for 21 days, and deaths were recorded. Sera were collected prior to immunizations to establish baseline exposures, and also following the full immunization protocol (but before challenge) in order to correlate circulating antibody to the 37-kDa protein with protection. The results obtained were as follows:

Days post challenge

1: no deaths

2: three control mice dead

3: two control mice dead

4: two control mice dead, one control mouse sick

5: one control mouse dead

6–21: no mouse deaths

Immunized with 37-kDa protein: 10/10 survived

Controls with no protein 2/10 survived (8/10 died)

Difference statistically significant: (p 0.0008) Rank sum test.

Example 5

Twenty CBA/CaHN/J mice carrying the xid mutation were injected according to the following protocol:

(1) All mice were bled prior to immunization to establish baseline immunity. Ten test mice were immunized subcutaneously in four sites with a total of 21 pg of 37-kDa protein antigen (pneumococcal fimbrial protein A) emulsified in Complete Freund's adjuvant (CFA). Ten control mice were immunized identically with CFA and buffer substituting for the antigen.

(2) Fourteen days later, the mice were boosted intraperitoneally (IP) with 100 µg of the 37-kDa protein antigen (test mice) or with buffer (controls). No adjuvant was used with this booster immunization.

(3) Eight days later, all mice were bled via the infraorbital sinus and they were collected and pooled into the two groups (immunized and controls). At the same time, blood was collected from individual mice to assay for antibody responses.

(4) One day later, two additional mice were injected intraocularly with 0.1 ml of pooled immune sera to attempt to passively transfer immunity. Three additional mice were injected intraperitoneally (IP) with 0.1 ml of pooled control mouse sera. (Only five mice were injected at this step because of the small amount of sera obtained from the immunized mice.)

(5) One hour after the IP injections, these five mice were challenged intravenously (iv) with 140 colony-forming units (cfu) of a mid-log phase *S. pneumoniae* type 3 strain, WU2.

(6) At the same time, the eighteen (8 test and 10 control) mice were challenged iv with the same culture of WU2.

(7) Deaths were tallied daily.

| RESULTS: | No. Dead/Total No. Challenged |
|---|---|
| Immunized with the 37-kDa protein: | 0/8 |
| Control mice: | 10/10 |
| Passive Protection: | |
| Mice receiving immune sera. | 0/2 |
| Mice receiving control sera. | 3/3 |

Mice immunized with the 37-kDa protein were protected from fatal challenge with strain WU2; this immunity could be passively transferred with sera from immunized mice. (Originally 10 test mice were used. However, two of these mice died of other causes prior to being challenged with WU2.)

Example 6

An enzyme-linked immunosorbent assay (ELISA) was developed using purified *S. pneumoniae* 37-kDa protein antigen, as a capture for human antibodies. Paired sera were tested from children, less than 24 months of age, known to have pneumococcal pneumonia. Disease confirmation was determined by blood culture or antigen in the urine. It was found that 35% (9/26) had antibody titers greater than sera from non-ill children of the same age group, p=0.06. This illustrates that some of the children responded to the 37-kDa protein antigen after natural infection.

Example 7

Preparation of the 37-kDa Protein or Polypeptide Conjugate

Conjugates can be prepared by use of a carrier protein bound to the 37-kDa protein or polypeptides derived from the 37-kDa protein via a linker, to elicit a T-cell dependent response. Such carrier proteins could be any immunogenic protein such as, for example, keyhole limpet hemocyanin bovine serum albumin, tetanus toxoid, diphtheria toxoid, or bacterial outer membrane proteins. Examples of bacterial outer membrane proteins, useful as conjugates, include outer membrane proteins of *Neisseria meningitidis* and *Haemophilus influenzae*. *Neisseria meningitidis* can be selected from *Neisseria meningitidis*, group A, B, or C. In addition, the 37-kDa protein or polypeptides thereof can be used in a conjugate where the 37-kDa protein or polypeptides thereof are the T-cell dependent immunogenic carrier for polysaccharide antigens that are B-cell stimulators. This is based on the theory that polysaccharide antigens are B-cell stimulators and that protective immunity is usually generated by a combination of B-cell and T-cell stimulation. Protein antigens exhibit T-cell dependent properties (i.e., booster and carrier priming). T-cell dependent stimulation is important because most children less than two years of age do not respond to T-cell independent antigens. The attachment or conjugation of antigens can be accomplished by conventional processes, such as those described in U.S. Pat. No. 4,808,700, involving the addition of chemicals that enable the formation of covalent chemical bonds between the carrier immunogen and the immunogen. In use, the 37-kDa protein antigen of this invention can be administered to mammals, especially humans, in a variety of ways. Exemplary methods include parenteral (subcutaneous) administration given with a nontoxic adjuvant, such as an alum precipitate or peroral administration given after reduction or ablation of gastric activity, or in a pharmaceutical form that protects the antigen against inactivation by gastric juice (e.g., a protective capsule or microsphere). The dose and dosage regimen will depend mainly upon whether the antigen is being administered for therapeutic or prophylactic purposes, the patient, and the patient's history. The total pharmaceutically effective amount of antigen administered per dose will typically be in the range of about 2 µg to 50 µg per patient. For parenteral administration, the antigen will generally be formulated in a unit dosage injectable form (solution, suspension, emulsion) in association with a pharmaceutically acceptable parenteral vehicle. Such vehicles are inherently nontoxic and nontherapeutic. Examples of such vehicles include water, saline, Ringer's solution, dextrose solution, and 5% human serum albumin. Non aqueous vehicles, such as fixed oils and ethyl oleate, may also be used. Liposomes may be used as vehicles. The vehicle may contain minor amounts of additives, such as substances which enhance isotonicity and chemical stability (e.g., buffers and preservatives).

Example 8

Bacterial strains. All isolates of *S. pneumoniae* were provided and serotyped by the Streptococcal Reference Laboratory, Division of Bacterial and Mycotic Diseases, National Center for Infectious Diseases, Centers for Disease Control and Prevention (CDC). The pneumococcal serotype 6B strain used for cloning and sequencing was a CDC reference strain (SP-86). *E. coli* DH5α (Bethesda Research Laboratories, Gaithersburg, Md.) was used as the recipient host for plasmids (pUC19 and its derivatives). *S. pneumoniae* strains were grown on Trypticase soy agar plates with 5% sheep blood cells or, where indicated, in Todd-Hewitt broth containing 0.5% yeast extract. *E. coli* cultures were grown in Luria broth which, when required, was supplemented with 100 pg/ml of ampicillin (Sigma Chemical Co., St Louis, Mo.).

Cloning and sequencing of the PsaA gene from *S. pneumoniae*, serotype 6B. A chromosomal library from *S. pneumoniae* serotype 6B was prepared as previously described. (Sampson et al., 1994. "Cloning and nucleotide sequence analysis of PsaA, the *Streptococcus pneumoniae* gene encoding a 37-kilodalton protein homologous to previously reported *Streptococcus* sp. adhesins," *Infect. Immun.*, 62:319–324), except that pUC18 was used as the cloning vector instead of pUC 13. Recombinants were screened by colony immunoblot using monoclonal antibody 1 E7. (Russell et al., 1990, "Monoclonal antibody recognizing a species-specific protein from *Streptococcus pneumoniae*," *J. Clin. Microbiol.* 28:2191–2195). This procedure and plasmid purification from positive clones (Ish-Horowicz et al. 1981, "Rapid and efficient cosmid cloning," *Nucleic Acids Res.* 9:2989–2998) and restriction endonuclease analysis, have all been previously described, (Sampson et al., 1990, "Nucleotide sequence of htpB, the *Legionella pneumophila* gene encoding the 58-kilodalton (kDa) common antigen, formerly designated the 60-kDa common antigen," *Infect Immun.* 58:3154–3157; and Sampson at al., 1994). Sodium dodecyl sulfate-polyacrylamide gel electrophoresis (SDS-PAGE) and Western blot analysis were done as before (Sampson et al., 1990). All other DNA manipulations were done according to methods described in Sambrook et al. DNA sequencing was performed using the ABI PRISM Dye Terminator Cycle Sequencing kit and procedure (Perkin-Elmer, Cetus, Foster City, Calif. Sequence data were analyzed with the DNASTAR software program (DNASTAR, Inc., Madison, Wis.) and the Wisconsin Genetics Computer Group sequence analysis software program (Fenno et al., 1989, "Nucleotide sequence analysis of a type 1 fimbrial gene of *Streptococcus sanguis* FW213," *Infect. Immun.* 57:3527–3533).

Preparation of genomic DNA for PCR-RFLP analysis. High molecular weight pneumococcal DNA was prepared by the procedure of Graves et al., 1993, "Universal bacterial DNA isolation procedure," p. 617–621, in D. H. Pershing et al. (ed), *Diagnostic molecular biology*, American Society for Microbiology, Washington, D.C.) with modifications. Sixteen-hour cultures of type specific *S. pneumoniae* were grown in 50 ml of Todd-Hewitt broth containing 0.5% yeast extract in screw cap flasks at 37° C. without shaking. Cultures were pelleted at 8000×g for 15 min at room temperature and washed with phosphate-buffered saline (10 mM, pH 7.2). The cell pellet was solubilized in 2.5 ml of buffer composed of 10 mM Tris, 1.0 mM EDTA, pH 8.0, and 0.4% SDS. Fifteen microliters of proteinase K (20 mg/ml) was added, and the lysate was incubated at 37° C. for 1 h. The mixture was adjusted to 0.48 M NaCl with the addition of 500 μl of 5M NaCl and, after mixing by inversion, 400 μl of 10% hexadecyltrimethylammonium bromide in 0.7% NaCl was added. This suspension was mixed as before, incubated for 30 min at 65° C., and extracted with an equal volume of phenol-chloroform-isoamyl alcohol. The upper aqueous phase was separated by centrifugation at 1500×g and extracted with chloroform-isoamyl alcohol. DNA was precipitated from the upper aqueous phase with 2.5 volumes of ethanol at −70° C. for 30 min. It was pelleted and dried in a desiccator, resuspended in water and quantitated by measuring absorbance at 260 nm.

PCR-RFLP. Restriction enzymes EcoRI, HinfI, MaeIII, MboII, MnlI, and NheI were obtained from Boehringer Mannheim Biochemicals (Indianapolis, Ind.); RsaI, Tsp509I, Eco57I. and XmnI were purchased from New England Biolabs (Beverly, Mass.). Primer sequences for the amplification reaction were selected from the N-terminal (nucleotides 181–201) and C-terminal (nucleotides 1106–1126) sequences of the *S. pneumoniae* serotype 6B gene (P1, AGGATCTAATGAAAAAATTAG (SEQ ID NO:3); P2. TCAGAGGCTTATTTTGCCAAT (SEQ ID NO:4)) and flanking regions. The primers were synthesized using standard procedures.

(i) DNA amplification. The reactions were performed with the Perkin-Elmer PCR amplification kit. Reaction volumes were 100 μl and contained the standard 1× reaction buffer without Mg, 1 μM of each primer, 2.0 mM $MgCl_2$, 0.2 mM dNTPs, template DNA, and 2.5 UT of Taq DNA polymerase. The source of the template DNA was either extracted purified chromosomal DNA or a bacterial colony. Conditions for amplification were as follows: 30 cycles of denaturation 94° C., 1 min, annealing 52° C., 0.5 min, and extension 72° C., 1.5 min. Amplified products were separated on a 1% agarose gel and visualized with ethidium bromide. A direct colony amplification procedure was adapted, which shortened template preparation by eliminating the necessity of extracting chromosomal DNA. The procedure consisted of adding a single bacterial colony directly from the plate into the PCR reaction mixture and heating at 95° C. for 10 minutes. The remaining PCR steps were performed as outlined for extracted chromosomal DNA and are given above.

(ii) Enzyme digestion. Digestion of amplified products was performed as directed by the manufacturer for the designated enzymes in volumes of 20 μl. Digestion products were analyzed by agarose (2% Metaphor agarose, FMC Corp., Rockland, Me.) gel electrophoresis and visualized after being stained with ethidium bromide.

Analysis of type 6B PsaA. Genomic DNA was partially digested by Sau3AI was ligated to BamHI-digested pUC18 and used to transform *E. coli* DH5α. Recombinant colonies were selected for resistance to ampicillin and the formation of white colonies in the presence of isopropyl-β-galactopyranoside (IPTG) and 5-bromo-4-chloro-3-indolyl-β-D-galactopyranoside. Colony immunoblot screening (using anti-PsaA MAb) of approximately 2,500 colonies yielded two positive clones, which were selected, purified, and rescreened by Western blot analysis using the same MAb. They both expressed a protein reactive with MAb to PsaA and which migrated in SDS-PAGE with the expected molecular mass of approximately 37-kDa. One was selected for continued study and was designated pSTR6. Limited restriction enzyme analysis of DNA from the recombinant plasmid showed that the positive clone contained an insert that was 3.5 kb with sites for enzymes ClaI, EcoRI, and HindIII. To localize the PsaA coding region, the insert was double digested with SstI (multiple cloning site in vector) and HindIII. The resultant fragments were ligated into pUC18 and transformed into *E. coli* DH5α. This generated a recombinant containing an insert of about 1.3 kb in size. The resultant subclone pSTR6y, when analyzed by SDS-PAGE and Western blot using anti-PsaA MAb, was shown to express full length PsaA immuno-reactive protein. The complete nucleotide sequence on both strands of the 1.3-kb insert was determined by cycle sequencing of the plasmid subclone using oligonucleotide primers complementary to the sequence. These were made as sequence information became available. The nucleotide sequence of the entire streptococcal insert is set forth in the Sequence Listing as SEQ ID NO:1. The single open reading frame (ORF) present, beginning at nucleotide 189 and ending at nucleotide 1,117, encodes the PsaA gene sequence. This ORF is 930 nucleotides long and when amplified and subcloned into vector systems such as pGEM (Promega, Madison, Wis.) and BAC-to-BAC™ expression system (Bethesda Research Laboratories, Gaithersburg, Md.) expresses full-length PsaA, reactive with anti-PsaA MAb antibodies. This ORF encodes a peptide of 309 amino acids with a deduced molecular weight of 34,598 and an isoelectric point of 5.23. Analysis of the peptide using the algorithm of Kyte et al., 1982, ("A simple method for displaying the hydropathic character of a protein," *J. Mol. Biol.* 157:105–132.) shows that the peptide contains a major hydrophobic region of 20 amino acids which encodes a putative leader sequence. This leader contains the consensus sequence for signal peptidase cleavage (LXXC) (SEQ ID NO: 12). Removal of this leader would result in a peptide of molecular mass 32,465 with a predicted isoelectric point of 4.97. A consensus sequence for a ribosomal binding site (Shine et al., 1974, "The 3'-terminal sequence of *E. coli* 16S ribosomal RNA: complementarity to nonsense triplets and ribosomal binding sites," *Proc. Natl. Acad. Sc. USA* 71:1324–1346) is located 5 nucleotides upstream of the ATG start codon.

Comparison of the serotype 6B sequence with streptococcal homologs. Comparison of the serotype 6B PsaA nucleotide sequence (Bilofsky et al., 1988, A GenBank genetic sequence database, Nucleic Acids Res. 16:1861–1864) (GenBank accession number U53509) and its flanking regions with the previously published strain R36A PsaA sequence (Sampson et al., 1994, "Cloning and nucleotide sequence analysis of PsaA, the *Streptococcus pneumoniae* gene encoding a 37 kilodalton protein homologous to previously reported *Streptococcus* sp. adhesins" *Infect. Immun* 62:319–324) shows the differences between the nucleotide sequences. The computed homology between the two sequences is 74%. Major areas of discord are in regions upstream and downstream of the ORF and in the initial 60 nucleotide which encode the putative signal peptide. When the two PsaA coding sequences are compared, the sequence homology increases to 78%. Serotype 6B sequence was also compared to the PsaA DNA sequence for another vaccine serotype, serotype 2, which was recently submitted to GenBank (Accession number U40786). Computer analysis of these two sequences shows that they are very similar, with computed DNA homology percentages of 99% between the two PsaA DNA sequences. There are eight single base differences between the two sequences. A comparison of serotype 2 and 6B PsaAs shows almost complete identity: the computed similarity value is 99.3. The eight base difference at the nucleotide level translated into a difference at the peptide level of six amino acids with two of the changes resulting in conservative substitutions. Further analyses and comparisons of the serotype 6B sequence to the other five GenBank PsaA homologues from viridans *Streptococci* and *E. faecalis* (Fenno et al., 1989, "Nucleotide sequence analysis of a type I fimbrial gene of *Streptococcus sanguis* FW213." *Infect. Immun.* 57:3527–3533; Sampson et al., 1994. "Cloning and nucleotide sequence analysis of PsaA, the *Streptococcus pneumoniae* gene encoding a 37-kilodolton protein homologous to previously reported *Streptococcus* sp. adhesins," *Infect. Immun.* 62:319–324: Ganeshkumar et al., 1991. "Nucleotide sequence of a gene coding for a saliva-binding protein (SsaB) from *Streptococcus sanguis* 12 and possible role of the protein in coaggregation with *actinomyces.*" *Infect. Immun.* 59:1093–1099, Kolenbrander et al., 1994. "Nucleotide sequence of the *Streptococcus gordonii* PK488 coaggregation adhesin gene scaA and ATP binding cassette." *Infect. Immun.* 62:4469–4480; and Lowe et al., 1995. "Cloning of an *Enterococcus faecalis* endocarditis antigen: homology with some adhesins from oral streptococci." *Infect. Immun.* 63:703–706) revealed significant sequence similarity between them. Sequence identities were 81%, 81%, 77%, 82%, and 57%, respectively, for PsaA (*S. pneumoniae* strain R36A), SsaB (*S. sanguis*), FimA (*S. parasanguis*), ScaA (*S. gordonii*) and EfaA (*E. faecalis*). Additionally, all six sequences showed great similarity in organization. They have a hydrophobic leader peptide containing the prolipoprotein consensus sequence LXXC (for signal peptidase II cleavage) (SEQ ID NO: 12) within the first 17–20 amino acids. This N-terminal leader sequence appears to represent the area of greatest variability. It is followed by a region of high similarity from amino acids 36 to 150. The region from 150 to 198 is a variable region and is followed by another conserved region (198 to 309).

PCR-RFLP analysis of chromosomal DNA from the 23 serotype strains in a 23-valent vaccine. PCR-RFLP was used to examine the degree of conservation of the gene among 23 *S. pneumoniae* serotypes, representing the 23 serotypes in a 23-valent vaccine. Since previous attempts to amplify pneumococcal type strains with primers corresponding to strain R36A were unsuccessful, primers for PCR were selected from N-terminal and C-terminal sequences of serotype 6B. Using primers complementary to serotype 6B, the PsaA gene from all 23 serotypes and subtypes represented in the 23-valent vaccine was amplified from chromosomal DNA. A total of 10 enzymes were chosen that had restriction endonuclease digestion sites throughout the entire length of the serotype 6B PsaA gene. Nine of the 10 enzymes give identical patterns for all 23 PsaA genes analyzed.

The one exception, restriction enzyme Tsp509I, had six sites within the gene and generated seven fragments upon digestion with sizes of 7, 30, 68, 146, 151,166, and 362 bp. When these fragments are separated on 2% metaphor agarose gel, a five-band pattern can be seen (7- and 30-bp fragments are not seen on these gels because of their small size). For 21 of 23 serotypes this five-fragment-enzyme pattern was obtained; but for strains of serotype 4 and 33F, the 146-bp fragment is absent and two new fragments appear flanking the 68-bp fragment making a total of seven bands. This increase in fragment number results from the presence of an extra Tsp509I site within the 146-bp fragment. To ascertain the prevalence of this extra site, the Tsp509I patterns of 3 to 4 additional strains of each of 23 serotype strains (additional strains of serotype 2 and serotype 25 were not available) were analyzed. All strains analyzed were random clinical isolates from the United States that had been submitted to CDC for serotyping. The majority of the 80 strains were blood isolates; exceptions were 2 from cerebrospinal fluid, 2 from pleural fluid, and 1 each from the eye and nose. Of the strains analyzed, 10% had the extra Tsp509I site, resulting in the altered RFLP pattern. This modification was seen only in types 4, 8, 11F, and 33F. In an attempt to determine the prevalence of this altered pattern, the PsaA gene from 8 additional strains of these 4 types was analyzed for the Tsp509I variation (bringing the total to 11–12 for these 4 types) Table 1 summarizes the analyses of serotypes 4, 8, 11A, and 33F. The modified pattern is sporadically present in serotypes 4 and 8, but is essentially always present in 11 of 12 strains of 11A and all strains of 33F. The occurrence of this pattern could not be correlated with geographic location or region of the United States since strains that showed variation came from diverse regions of the country. All strains of types 4, 8, 11A, and 33F were blood isolates except one 33F strain, which was a nasal isolate; thus the relevance of the site of isolation on prevalence of this modification could not be assessed.

TABLE 1

Screening of selected serotypes for additional Tsp509I restriction site

| Serotype | Ratio of serotypes with additional site to total no. of serotypes tested | | Total serotypes with unique patterns % |
|---|---|---|---|
| | Expt. #1[a] | Expt. #2[b] | Unique pattern |
| 4 | 1/3 | 3/9 | 33 (4/12)[c] |
| 8 | 3/4 | 4/9 | 44 (7/13) |
| 11A | 2/3 | 9/9 | 92 (11/12) |
| 33F | 3/3 | 9/9 | 100 (12/12) |

[a]Initial Tsp509I analysis which included survey of 2–3 strains each of all 23 vaccine types.
[b]Tsp509I analysis of more strains of types showing additional Tsp509I site.
[c]Shown in parenthesis is ratio of number with additional site to number tested.

This analysis discloses the cloning and sequencing of the gene encoding PsaA from *S. pneumoniae* serotype 6B and a subsequent analysis of the gene in the 23 pneumococcal polysaccharide vaccine serotypes. Sequence analysis revealed that the serotype 6B sequence and the previously published strain R36A were less similar than expected. The nucleotide sequence and its flanking regions were only 73% homologous to the original strain R36A PsaA, while the actual PsaA coding sequences had a computed homology of 78%. Protein sequence similarity between the two sequences was only 81%. A comparison of the serotype 6B sequence with the newly submitted serotype 2 pneumococcal PsaA (a vaccine serotype) gave computed DNA homology values of 99% and 98% protein sequence similarity. These values are evidence of the high sequence conservation for the gene within the vaccine serotypes. Moreover, when the deduced amino acid sequences of these two sequences were compared with other published sequences for PsaA homologues within the genus, large areas of similarity were evident for all five proteins. Similarity values within the group ranged from 57% to 82%.

The need for a *Streptococcus pneumoniae* vaccine candidate prompted us to clone and sequence the PsaA gene from *S. pneumoniae* serotype 6B. The heterogeneity between the two pneumococcal PsaA genes (6B and R36A) led us to examine the vaccine serotypes to determine the degree of diversity among strains. Primers homologous with the N terminus and C terminus of the serotype 6B sequence amplified all 23 of the vaccine serotypes PCR-RFLP analysis using 10 different restriction enzymes representing 21 sites within the serotype 6B gene and shows only one area of diversity, which resulted in an additional Tsp509I site for a small number of strains. This study demonstrates that the serotype 6B gene sequence is representative of the sequence found among the vaccine serotypes. Evidence for this includes the 99% DNA sequence identity between serotype 2 and serotype 6B and the uniform and identical restriction patterns covering the 21 sites examined in this study. It is clear that the earlier strain R36A PsaA sequence represents a variant sequence seemingly not present in the serotypes that were analyzed here since we were unable to amplify them using primers to strain R36A PsaA. The more important aspect of this study, however, is that there is limited diversity among the vaccine serotypes analyzed. These are the serotypes that cause disease and thus, the ones against which prophylactic measures are needed. The lack of genetic diversity of PsaA among these serotypes suggests that gene is highly conserved and is an excellent candidate for vaccine development.

Example 9

Monoclonal Antibodies

The 37-kDa protein from serotype 22F was used to generate monoclonal antibodies 1B6E12H9, 3C4D5C7, 4E9G9D3, 4H5C10F3, 6F6F9C8, and 8G12G11B10 (disclosed in U.S. patent application Ser. No. 08/715,131, incorporated herein by reference). The MAbs were analyzed for their ability to confer protection from infection by *Streptococcus pneumoniae*. Table 2 shows that of 5 monoclonal antibodies tested, one in particular gave efficient protection from subsequent *S. pneumoniae* challenge (8G12G11 B10). The protection from *S. pneumoniae* was dose-responsive. demonstrating that the monoclonal antibody was responsible for the protection (Table 3).

TABLE 2

Passive protection of five Anti-37-kDa monoclonal antibodies in an infant mouse model to *Streptococcus pneumoniae* serotype 6B.

| 37-kDa MAb Cell Line[a] | Bacteremia @ 48 h (%) | Death @ 48 h (%) | Death @ 14 d (%) |
|---|---|---|---|
| 1E7A3D7C2 | 100 | 100 | 100 |
| 8G12G11B10 | 100 | 0 | 20 |
| 4E9G9D3 | 100 | 80 | 100 |
| 6F6F9C8 | 100 | 60 | 100 |
| 1B6E12H9 | 100 | 80 | 100 |

[a]Challenge dose (1.7 × 10³ cfu) or 10x bacteremic dose 100% ($BD_{100}$). Five/mice group given 50 μg total antibody. All MAbs are IgG.

TABLE 3

Effect of a Second Dose on the Passive Protective Potential of the Anti-37-kDa Monoclonal Antibody 8G12G11B10.

| MAb Dose Level (μg) | | Bacteremia @ 48 h | | Death @ 48 h | Death @ 10 d |
|---|---|---|---|---|---|
| Pre | Post | % | Avg. cfu/ml | % | % |
| 50 | — | 100 | $1.2 \times 10^4$ | 0 | 30 |
| 50 | 50 | 80 | $1.0 \times 10^4$ | 0 | 50 |
| 5 | — | 100 | $4.7 \times 10^4$ | 70 | 100 |
| 5 | 5 | 100 | $3.0 \times 10^4$ | 50 | 80 |
| — | — | 100 | $>10^5$ | 80 | 100 |

[a]All infant mice were challenged with 10 × $BC_{100}$, (2 × 10³ cfu). Mab given 24 h prior to and 24 h after (post-) challenge. 10 mice/group.

Example 10

Phage Display Library

A phage display library containing inserts of 15 amino acid residues located at the N-terminal part of the pill coat protein (Parmley and Smith, 1988) was constructed in the phage FUSE 5 as vector. The library was made by ligating a synthetic 33 bp BglI fragment into FUSE 5 and transfecting *E. coli* Kq1/kan+cells by electroporation. The phage progeny contain the display library.

Example 11

Screening by Biopanning

Four cycles of biopanning were carried out for each of the MAbs employed in order to screen the phage library of the PsaA peptides prepared in Example 10 (Smith and Scott, 1993, *Meth. Enzymol.*, 217:228–257). The substrate of a Petri dish was coated with streptavidin and ten µg of biotinylated anti-PsaA MAb as prepared in Example 1. The remaining biotin binding sites were blocked with 1.5 ml of D-biotin (10 mM). The phage library ($10^{11}$ to $10^{12}$ transforming units) was then incubated with the immobilized MAb. Bound phage were eluted from the streptavidin coated plates with 0.1 N HCl, pH 2.2. The eluted phage were titrated and amplified, and then subjected to two further rounds of selection performed as above. The amount of biotinylated MAb used was 1 nM and 1 µM, respectively, in the second and third rounds, so that only high affinity peptides were bound by the end of the last cycle.

Example 12

Amino Acid Sequences of Immunogenic Peptides

High affinity specimens from the library obtained using the procedures of Example 11 were propagated and sequenced. For each MAb, ten phage specimens resulting from the selection process were sequenced. Approximately 1 µg of single-stranded DNA was purified by phenol and chloroform extraction, ethanol precipitated and resuspended in 7 µl water. Sequencing reactions were performed using a 27-mer primer complementary to the FUSE 5 vector sequence derived from a region in wild-type pIII common to all fd-tet derived vectors and $^{35}$S SEQUENASE® version 2 (U.S. Biochemicals, Cleveland, Ohio). The sequences obtained are shown in Table 4. They were compared to known sequences of PsaA strains 2 and 6B using Clusta IV and tFasta programs to identify the epitope on the PsaA with which each peptide is aligned most closely. These epitope positions are also given in Table 4. The peptide obtained using MAb's 8G12, 6F6, and 1E7 align to PsaA best when an additional residue is present on the protein where the gap appears after residue 13 of the peptide (SEQ ID NO: 7 and SEQ ID NO: 8).

TABLE 4

Peptide Sequences Obtained by Biopanning with MAbs

| MAb | Sequence | SEQ ID NO: | PsaA Res. Nos. |
|---|---|---|---|
| 4E9 | TVSRVPWTAWAFHGY | 5 | 132–136 |
| 1B6 | RSYQHDLRAYGFWRL | 6 | 206–220 |
| 8G12 | LVRRFV HRRPHVE-SQ | 7 | 252–267 |
| 6F6 | LVRRFVHHRPHVE-SQ | 8 | 252–267 |
| 1E7 | LVRRFVHHRPHVE-SQ | 8 | 252–267 |

Example 13

Immunization of Mice with Immunogenic Peptides of PsaA

Peptides having the sequences set out in SEQ ID NOs. 5, 6, 7, and 8 are to be synthesized in an automated peptide synthesizer. The peptides are to be purified by reversed phase HPLC, and the principal peak is to be collected. Their sequences are to be verified by automated peptide sequencing, using an automated sequencing apparatus such as that manufactured by Beckman Instruments, Inc., Mountain View, Calif. Each peptide is to be conjugated to keyhole limpet hemocyanin using coupling mediated by water-soluble carbodiimide reagent. The resulting conjugate is to be dissolved at a final concentration of about 180 µg/ml in phosphate buffered saline pH 7.2 and combined at an approximate 1:1 ratio in emulsion with Freund's incomplete adjuvant (Sigma Chemical Co., St. Louis, Mo.). BALB/c mice are to be initially immunized intraperitoneally with this suspension, and one month later, the mice are to be boosted with about 110 µg/ml conjugate without adjuvant.

Example 14

Immunization of Mice with a Consensus Peptide Identified by Phage Display

An investigation was performed of the ability of a peptide having a consensus sequence, SEQ ID NO:8, of several peptides identified by phage display to elicit an immunological response against PsaA. The consensus peptide (L V R R F V H R R P H V E S Q) (SEQ ID NO:7) determined from the peptides which bound monoclonal antibodies 8G12, 6F6 and 1E7 in the phage display experiments described in Example 12 above, was synthesized with a CYGG (SEQ ID NO: 11) spacer nd a lauroyl group to its amino terminal end (Bio-Synthesis, Lewisville, TX). The lauroyl group enhances the hydrophobic complexing of peptide groups to proteosomes (Lowell, G. H., et al., "Proteosomes, hydrophobic anchors, iscoms, and liposomes for improved presentation of peptide and protein vaccines," in: *New Generation Vaccines*, Woodrow, G. M., Levine, M. M. (Ed.), Marcel Dekker, Inc., New York, pp. 141–160 (1990); Lowell, G. H., et al., "Peptides bound to proteosomes via hydrophobic feet become highly immunogenic without adjuvants," *J. Exp. Med.* 167:658 (1988); and Zollinger, W. D., et al., "Complex of meningococcal group B polysaccharide and type 2 outer membrane protein immunogens in man," *J. Clin. Invest.* 63:836 (1979)). The cysteine group on the other hand enhances the immunogenicity of the peptide (Lowell, G. H., et al., (1990)). Proteosomes were prepared from the outer membrane complex vesicles from group *B. meningococci*, strain 99M as described by Zollinger (Zollinger, et al., (1990)). Synthetic lipopeptides were complexed to proteosomes on a 1:1 (w/w) ratio by combining the components in the presence of detergent. The detergent was removed by extensive dialysis (Lowell, G. H., et al., (1988)).

Three- to 4-week-old BALB/c mice (n=4 per group) were primed with 10, 25, and 50 µg peptide (SEQ ID NO:5) proteosome complex at Week 0. Mice in each group were then boosted with 10, 25, and 50 µg peptide (SEQ ID NO:5) proteosome complex at Weeks 2 and 3. Mice primed with 20 µg PsaA protein at Week 0 were a positive control for this study. The negative controls consisted of mice primed with 10, 25, and 50 µg proteosome at week 0 and boosted with 10, 25, and 50 µg proteosomes at Weeks 2 and 3. Sera was collected every week for 4 weeks and the anti-PsaA specific antibodies were tested by enzyme-linked immunoadsorbent assay (ELISA).

Anti-PsaA specific ELISA was performed as follows: Nunc immuno MaxiSorb™ plates were coated with 5 µg/ml of purified native PsaA protein at 4° C. overnight. Plates were washed with PBS/Tween buffer (PBS containing 0.01% TWEEN®-20) and blocked with PBS/Tween buffer containing 1% BSA. Serial dilutions of mouse sera starting at 1:10 in PBS/Tween/BSA were incubated for 1 h at 37° C. The plates were washed four times with PBS/Tween. Anti-mouse IgG and IgM conjugated to horseradish peroxidase (Sigma, St. Louis, Mo.), diluted at 1:4000 in PBS/Tween/BSA, were added to the plates. Anti-PsaA antibodies were detected with o-phenylenediamine substrate for 30 min in the dark. Absorbance was read at 490 nm on Microplate E1311 (Biotek, Winooski, Vt.).

The sequences of the peptides selected by MAb 8G12, 1E7, and 6F6 aligned to the same region of the PsaA molecule. One sequence from MAb 8G12 selected sequences and the sequences selected by 1E7 and 6F6 had the same insert (SEQ ID NO:8), as indicated above. The homology between these peptides and PsaA was determined to lie in 6 amino acids. This region was used to define the consensus peptide sequence (SEQ ID NO:8). This peptide was synthesized with an N-terminal Lauroyl group and CYGG motif to allow the complexing to proteosomes and improve immunogenicity. Mice were immunized with 10, 25, and 50 µg of the consensus peptide complexed to proteosomes. The sera from peptide immunized mice exhibited an anti-PsaA-response. Results of this study are shown in Tables 5 and 6. The peptide immunized mice developed an IgG response where the titers ranged from 159 to 252 at Week 4. The titers were calculated after normalizing the data for proteosome background values. Of the three dose groups, the immune response to the 50 µg peptide dose group was the highest. However the anti-PsaA response to the peptide is significantly lower (p<0.05) than immune response to the PsaA protein.

TABLE 5

IgM Titers Against PsaA

| IgM titer at 25% | Week 1 | Week 2 | Week 3 | Week 4 |
|---|---|---|---|---|
| 10 µg peptide (SEQ ID NO:8) | 130 | 130 | 178 | 338 |
| 25 µg Peptide (SEQ ID NO:8) | 197 | 237 | 109 | 102 |
| 50 µg Peptide (SEQ ID NO:8) | 215 | 171 | 229 | 265 |
| PsaA | 169 | 87 | 322 | 443 |

The data is represented as 25% titer of the control sera from mice immunized with 20 µg PsaA.

TABLE 6

IgG Titers Against PsaA

| IgG titer at 25% | Week 1 | Week 2 | Week 3 | Week 4 |
|---|---|---|---|---|
| 10 µg peptide (SEQ ID NO:8) | 96 | 70 | 111 | 159 |
| 25 µg Peptide (SEQ ID NO:8) | 93 | 154 | 188 | 193 |
| 50 µg Peptide (SEQ ID NO:8) | 120 | 64 | 155 | 252 |
| PsaA | 260 | 150 | 4919 | 40897 |

As in Table 2, the data is represented as 25% titer of the control sera from mice immunized with 20 µg PsaA.

Example 15

Immunization of Mice with a Lipidated and Unlipidated Form of a Peptide Identified by Phage Display. [The Data in this Example are from Srivastava, N., et al., "Selection of an Immunogenic . . . ," Hybridoma 19:23 (2000)]

An investigation was performed of the ability of the peptide having the amino acid sequence as described in SEQ ID NO:5 (T V S R V P W T A W A F H G Y) encoded by the phage selected by MAb 4E9, to protect mice from S. pneumoniae challenge. Two forms of the peptide were synthesized. One form was synthesized with a palmitoyl residue at its N-terminal end and will be referred to as SEQ ID NO:5-lipidated. Another form was the same peptide without any ligands and is referred to as SEQ ID NO:5-unlipidated. These peptides were synthesized using an ACT model 396 HPS peptide synthesizer (Advanced ChemTech, Louisville, Ky.) using solid phase F-moc chemistry as described by Stewart et al., "Solid peptide synthesis, $2^{nd}$ ed., Pierce Chemical Co., Rockford, Ill. (1984). Lipidated versions of the peptides described above containing monopalmitic acid were synthesized by coupling palmitic acid (Sigma Chemicals, St. Louis, Mo.) to the deprotected amino-terminus of the resin-bound peptide employing the same reaction conditions as for the standard amino acid couplings described above (Verhaul et al. (1995)). Sequences were verified by automated peptide sequencing using a Porton model #2090 automated peptide sequencer (Beckman Instruments, Inc., Mountain View, Calif.). Peptides were suspended in phosphate buffered saline pH 7.2 (PBS) to final concentrations of 1.0 mg/ml for initial dose and 0.5 mg/ml for subsequent doses.

To analyze the ability of the peptide SEQ ID NO:5-lipidated and SEQ ID NO:5-unlipidated to protect against S. pneumoniae challenge, ten-week-old ND-4 mice (Swiss Webster) were immunized on a three-dose regimen. Test mice (n=15 for each peptide) received an initial dose at Day 0 of 100 µg followed by booster doses at 3 and 5 weeks of 50 µg of the appropriate peptide. The peptide SEQ ID NO:5-lipidated was suspended in 100 µl PBS 0.01 M, pH 7.2, while the unlipidated peptide SEQ ID NO: 5-unlipidated, was mixed with the adjuvant ALHYDROGEL® (2%; #A1090BS, Accurate Chemical and Scientific Company, Westbury, N.Y.) at 6.3 mg/ml in PBS to enhance the immunogenicity of the peptide. Control mice (n=12) were similarly immunized but without peptide. Each mouse was immunized subcutaneously between the shoulders. One week following the final boost, all mice were challenged with $4.9 \times 10^6$ cfu of S. pneumoniae, strain PLN-D39 (kindly provided by James Paton, Women's and Children's Hospital, North Adelaide, S.A. Australia), a pneumolysin-negative derivative of D39. This was followed 5 days later by euthanasia and culturing of nasal washes. PBS nasal washes were done by the method of Wu, H. Y., et al., ("Establishment of a Streptococcus pneumoniae nasopharyngeal colonization model in adult mice," Microb. Pathog. 23:127 (1997)). The wash was diluted 3x out to a final dilution of 1:486. Fifty microliters of each dilution was cultured on blood agar+gentamicin plates (Trypticase soy agar supplemented with 5% defibrinated sheep a blood and 0.5% gentamicin). Data from NP colonization and carriage in immunized mice and placebo (PBS-immunized controls) were analyzed using either the t-test or the Mann-Whitney rank sum test. Nasopharyngeal carriage is the number of colony forming units per nose. Nasopharyngeal colonization is either positive or negative for a mouse depending on whether at least 1 cfu forms in 25 µl of nasal wash.

To analyze the ability of the peptide SEQ ID NO:5-lipidated and SEQ ID NO:5-unlipidated to protect against S. pneumoniae challenge, Swiss Webster mice were immunized with SEQ ID NO:8-lipidated, SEQ ID NO:8-unlipidated, and PsaA as described above. Mice immunized with the peptide SEQ ID NO:8-lipidated demonstrated a statistically significant reduction (p<0.05) in the bacterial nasal carriage when compared to placebo controls (Table 7). In addition, mice immunized with peptide SEQ ID NO:8-lipidated had a 40% greater chance of resisting colonization with S. pneumoniae serotype 2 (Table 7). This was statistically significant (p<0.05, Fisher's exact test, two-tailed) when compared to the placebo controls. A reduction in pneumococcal nasal colonization was seen in mice immunized with the nonlipidated peptide SEQ ID NO:8-unlipidated; however, this reduction was not statistically significant (p=0.48) when compared with the placebo control (Table 7).

TABLE 7

Summary of Protection Studies in Swiss-Webster Mice*

| Peptide | Carriage-geometric mean (cfu/nose) | Colonization no./total (%) | p-Values |
|---|---|---|---|
| SEQ ID NO:5-Lipidated** | 41 | 9/15 (60) | 0.048 |
| SEQ ID NO:5-Unlipidated | 205 | 13/15 (87) | 0.48 |
| Control | 460 | 12/12 (100) | — |

*The data are represented as geometric mean of the carriage (cfu/nose) of three experiments. Colonization is defined as 1 cfu/25 µl of nasal wash. The significance is computed using Mann-Whitney U rank sum test (p < 0.05).
**Lipidated with monopalmitic acid on an N-terminal additional cysteine residue. The lipidated peptides contained the amino acid sequence CSS bound to the amino terminus of the amino acid sequence from the sequence listing indicated such that the cystein (C) residue is at the amino terminus of the peptide.

Example 16

Immunization of Mice with Multiple Antigenic PsaA Peptides

The ability of peptides having a sequence given by SEQ ID NO:5, SEQ ID NO:6, and SEQ ID NO:7 to protect mice from an *S. pneumoniae* challenge, when administered separately, in lipidated or multiple antigenic peptides (MAPS) forms, or in conjunction with one-another on MAPS, was investigated. Peptides having the sequence given by SEQ ID NO: 5, 6, and 7 were synthesized using similar reagents, equipment, and procedures as described in Example 15. Multiple antigenic peptides (MAPS) containing either two arms, three arms, or four arms (FIG. 1) were synthesized according to the methods of Tam, J. P., "Multiple antigenic peptide system: A novel design for synthetic peptide vaccines and immunoassay. In *Synthetic Peptides: Approaches to Biological Problems*, J. P. Tam and E. T. Kaiser, eds., Alan R. Liss, Inc., New York, 3–18 (1989). All MAPS discussed in this Example contain an additional norleucine (NLe) residue on the carboxy terminus to facilitate synthesis (FIG. 1). Alum was added to the suspension for the non-lipidated peptides.

Separate groups of ND4 mice (n=8 per peptide and control group) were immunized subcutaneously three times at weeks 0, 3, and 5 with 100 µg, 50 µg, and 50 pg, respectively, of both the non-lipidated and lipidated peptides. One week after the third dose, mice were challenged intranasally (IN) with $10^6$ cfu of either serotype 2, 4, or 6B of *Streptococcus pneumoniae* suspended in 10 µl of 0.85% physiological saline. This was followed 5 days later by euthanasia and culturing of nasal washes. Nasopharyngeal (NP) colonization and carriage were analyzed as described in Example 15.

Immunizations with non-lipidated and lipidated, mono-peptide (i.e., homogeneous) and bi-peptide MAPS (i.e., heterogeneous MAPS comprising 2 different peptide sequences) resulted in an immunological response to *S. pneumoniae* challenge. This immunological response was evidenced by in vivo protection (i.e., reduction of cfu's) against intra-nasal carriage. The strongest immunological response was observed with immunizations of bi-peptide MAPS. Reduction in NP colonization was observed in, and varied among, the lipidated and non-lipidated peptides and the various MAP constructs. Immunizations with non-lipidated mono-peptide (i.e., homogeneous) MAPS resulted in a reduction of NP colonization of between 40 and 93 percent (Table 8). Immunization with lipidated mono-peptides resulted in NP colonization reduction of between 48 and 94 percent. The greatest reduction in carriage was observed with bi-peptide MAPS. Immunization of non-lipidated bi-peptide MAPS resulted in NP colonization reduction of between 68 and 91 percent (Table 9). This reduction in NP colonization observed with immunization of bi-peptide MAPS was statistically significant (p<0.05) for all serotypes and bi-peptides tested.

PsaA peptides used in this experiment, identified by phage display analysis using monoclonals against PsaA, are immunogenic and reduce carriage of the 3 serotypes of *S. pneumoniae* tested. Furthermore, bi-peptide MAPS were more effective in reducing carriage than mono-peptide MAPS.

TABLE 8

Percent reduction in naso-pharyngeal (NP) colonization: non-lipidated four-arm homogeneous MAPS compared to controls (P-value)

| | | Serotype | | |
|---|---|---|---|---|
| Peptide | Type* | 2(PLN-D39) | 4 | 6B |
| 4-arm MAP 5*** | NL | 67(.04**) | 93(<.01) | 64(.11) |
| 4-arm MAP 6**** | NL | 40(.24) | 88(<.01) | 47(.13) |
| 4-arm MAP 7***** | NL | 40(.20) | 42(.49) | 81(.03**) |

*Non-lipidated peptide (NL).
**Statistically significant difference (P ≤ 0.05) from controls as computed by the t-test or Mann-Whitney rank sum test.
***Homogeneous 4 arm MAP of SEQ ID NO:5.
****Homogeneous 4 arm MAP of SEQ ID NO:6.
*****Homogeneous 4 arm MAP of SEQ ID NO:7.

TABLE 9

Percent reduction in NP colonization of lipidated peptides and bi-peptide MAPS of the current invention compared to controls*

| Peptide | Sero-type: | 2 | 4 | 6B |
|---|---|---|---|---|
| SEQ ID NO:5-lipidated** | | 52(.13) | 74(.05) | 63(.02) |
| SEQ ID NO:6-lipidated** | | 64(.11) | 94(.02) | 58(.01) |
| SEQ ID NO:7-lipidated** | | 65(.20) | 82(<.01) | 48(.20) |
| 4-arm MAP 5–6*** | | 78(.03) | 82(<.01) | 91(<.01) |
| 4-arm MAP 5–9**** | | 87(<.01) | 82(<.01) | 68(.02) |

*(P-value)
**Lipidated with monopalmitic acid on an N-terminal additional cysteine residue. The lipidated peptides contained the amino acid sequence CSS bound to the amino terminus of the amino acid sequence from the sequence listing indicated such that the cystein (C) residue is at the amino terminus of the peptide.
***Heterogeneous 4 arm MAP of SEQ ID NO:5 and SEQ ID NO:6, as shown in FIG. 1A.
****Heterogeneous 4 arm MAP of SEQ ID NO:5 and SEQ ID NO:9, as shown in FIG. 1B.

Example 17

Immunization of Mice with Tripeptide MAPS

Tripeptide three-arm MAPS should also provide protection from *S. pneumoniae* challenge. Tripeptide three-arm MAPS can be synthesized which contain a first arm having the sequence given as SEQ ID NO:5, a second arm having the sequence given by SEQ ID NO:9, and a third arm having the sequence given by SEQ ID NO:10 (FIG. 1C) using similar reagents, equipment, and procedures as described in Examples 15 and 16. When tested using procedures similar to Examples 15 and 16, such tripeptide three-arm MAPS are expected to also provide protection from *S. pneumoniae* challenge.

We claim:

1. An isolated multiple antigenic peptide, wherein the multiple antigenic peptide has at least one first arm comprising the amino acid sequence of SEQ ID NO: 5, at least one second arm comprising the amino acid sequence of SEQ ID NO: 6, and at least one third arm comprising the amino acid sequence of SEQ ID NO: 7.

* * * * *

SEQUENCE LISTING

<160> NUMBER OF SEQ ID NOS: 12

<210> SEQ ID NO 1
<211> LENGTH: 1330
<212> TYPE: DNA
<213> ORGANISM: Artificial Sequence
<220> FEATURE:
<221> NAME/KEY: CDS
<222> LOCATION: (189)...(1115)
<223> OTHER INFORMATION: Description of Artificial Sequence; note = synthetic construct

<400> SEQUENCE: 1

```
tactgcttca gttttgggac tctttattgg ctatagtttt aatgttgcgg caggttcatg      60
tatcgtgctt acagctgcta gtttctttct cattagcttc tttatcgctc ccaaacaacg     120
atatttgaaa ctgaaaaata aacatttgtt aaaataaggg gcaaagccct aataaattgg     180 aggatcta atg aaa aaa tta ggt aca tta ctc gtt ctc ttt ctt tct gca     230
         Met Lys Lys Leu Gly Thr Leu Leu Val Leu Phe Leu Ser Ala
           1               5                  10 atc att ctt gta gca tgt gct agc gga aaa aaa gat aca act tct ggt     278
Ile Ile Leu Val Ala Cys Ala Ser Gly Lys Lys Asp Thr Thr Ser Gly
 15                  20                  25                  30 caa aaa cta aaa gtt gtt gct aca aac tca atc atc gct gat att act     326
Gln Lys Leu Lys Val Val Ala Thr Asn Ser Ile Ile Ala Asp Ile Thr
             35                  40                  45 aaa aat att gct ggt gac aaa att gac ctt cat agt atc gtt ccg att     374
Lys Asn Ile Ala Gly Asp Lys Ile Asp Leu His Ser Ile Val Pro Ile
         50                  55                  60 ggg caa gac cca cac gaa tac gaa cca ctt cct gaa gac gtt aag aaa     422
Gly Gln Asp Pro His Glu Tyr Glu Pro Leu Pro Glu Asp Val Lys Lys
     65                  70                  75 act tct gag gct gat ttg att ttc tat aac ggt atc aac ctt gaa aca     470
Thr Ser Glu Ala Asp Leu Ile Phe Tyr Asn Gly Ile Asn Leu Glu Thr
 80                  85                  90 ggt ggc aat gct tgg ttt aca aaa ttg gta gaa aat gcc aag aaa act     518
Gly Gly Asn Ala Trp Phe Thr Lys Leu Val Glu Asn Ala Lys Lys Thr
 95                 100                 105                 110 gaa aac aaa gac tac ttc gca gtc agc gac ggc gtt gat gtt atc tac     566
Glu Asn Lys Asp Tyr Phe Ala Val Ser Asp Gly Val Asp Val Ile Tyr
                115                 120                 125 ctt gaa ggt caa aat gaa aaa gga aaa gaa gac cca cac gct tgg ctt     614
Leu Glu Gly Gln Asn Glu Lys Gly Lys Glu Asp Pro His Ala Trp Leu
            130                 135                 140 aac ctt gaa aac ggt att att ttt gct aaa aat atc gcc aaa caa ttg     662
Asn Leu Glu Asn Gly Ile Ile Phe Ala Lys Asn Ile Ala Lys Gln Leu
        145                 150                 155 agc gcc aaa gac cct aac aat aaa gaa ttc tat gaa aaa aat ctc aaa     710
Ser Ala Lys Asp Pro Asn Asn Lys Glu Phe Tyr Glu Lys Asn Leu Lys
    160                 165                 170 gaa tat act gat aag tta gac aaa ctt gat aaa gaa agt aag gat aaa     758
Glu Tyr Thr Asp Lys Leu Asp Lys Leu Asp Lys Glu Ser Lys Asp Lys
175                 180                 185                 190 ttt aat aag atc cct gct gaa aag aaa ctc att gta acc agc gaa gga     806
Phe Asn Lys Ile Pro Ala Glu Lys Lys Leu Ile Val Thr Ser Glu Gly
                195                 200                 205 gca ttc aaa tac ttc tct aaa gcc tat ggt gtc cca agt gcc tac atc     854
Ala Phe Lys Tyr Phe Ser Lys Ala Tyr Gly Val Pro Ser Ala Tyr Ile
            210                 215                 220
```

-continued

```
tgg gaa atc aat act gaa gaa gaa gga act cct gaa caa atc aag acc    902
Trp Glu Ile Asn Thr Glu Glu Glu Gly Thr Pro Glu Gln Ile Lys Thr
            225                 230                 235 ttg gtt gaa aaa ctt cgc caa aca aaa gtt cca tca ctc ttt gta gaa    950
Leu Val Glu Lys Leu Arg Gln Thr Lys Val Pro Ser Leu Phe Val Glu
    240                 245                 250 tca agt gtg gat gac cgt cca atg aaa act gtt tct caa gac aca aac    998
Ser Ser Val Asp Asp Arg Pro Met Lys Thr Val Ser Gln Asp Thr Asn
255                 260                 265                 270 atc cca atc tac gca caa atc ttt act gac tct atc gca gaa caa ggt   1046
Ile Pro Ile Tyr Ala Gln Ile Phe Thr Asp Ser Ile Ala Glu Gln Gly
                275                 280                 285 aaa gaa ggc gac agc tac tac agc atg atg aaa tac aac ctt gac aag   1094
Lys Glu Gly Asp Ser Tyr Tyr Ser Met Met Lys Tyr Asn Leu Asp Lys
            290                 295                 300 att gct gaa gga ttg gca aaa taagcctctg aaaaacgtca ttctcatgtg      1145
Ile Ala Glu Gly Leu Ala Lys
            305 agctggcgtt ttttctatgc ccacatttcc ggtcaaatca ttggaaaatt ctgactgttt 1205 cagatacaat ggaagaaaaa agattggagt atcctatggt aacttttctc ggaaatcctg 1265 tgagctttac aggtaaacaa ctacaagtcg gcgacaaggc gcttgatttt tctcttacta 1325 caaca                                                            1330

<210> SEQ ID NO 2
<211> LENGTH: 309
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Met Lys Lys Leu Gly Thr Leu Leu Val Leu Phe Leu Ser Ala Ile Ile
 1               5                  10                  15

Leu Val Ala Cys Ala Ser Gly Lys Lys Asp Thr Thr Ser Gly Gln Lys
             20                  25                  30

Leu Lys Val Val Ala Thr Asn Ser Ile Ile Ala Asp Ile Thr Lys Asn
         35                  40                  45

Ile Ala Gly Asp Lys Ile Asp Leu His Ser Ile Val Pro Ile Gly Gln
     50                  55                  60

Asp Pro His Glu Tyr Glu Pro Leu Pro Glu Asp Val Lys Lys Thr Ser
 65                  70                  75                  80

Glu Ala Asp Leu Ile Phe Tyr Asn Gly Ile Asn Leu Glu Thr Gly Gly
                 85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu
    130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190
```

```
                                      -continued

Lys Ile Pro Ala Glu Lys Lys Leu Ile Val Thr Ser Glu Gly Ala Phe
        195                 200                 205

Lys Tyr Phe Ser Lys Ala Tyr Gly Val Pro Ser Ala Tyr Ile Trp Glu
    210                 215                 220

Ile Asn Thr Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
        275                 280                 285

Gly Asp Ser Tyr Tyr Ser Met Met Lys Tyr Asn Leu Asp Lys Ile Ala
    290                 295                 300

Glu Gly Leu Ala Lys
305

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
aggatctaat gaaaaaatta g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4
tcagaggctt attttgccaa t                                              21

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Thr Val Ser Arg Val Pro Trp Thr Ala Trp Ala Phe His Gly Tyr
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Arg Ser Tyr Gln His Asp Leu Arg Ala Tyr Gly Phe Trp Arg Leu
1               5                   10                  15
```

```
<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Leu Val Arg Arg Phe Val His Arg Arg Pro His Val Glu Ser Gln
  1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Leu Val Arg Arg Phe Val His His Arg Pro His Val Glu Ser Gln
  1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Leu Val Arg Arg Phe Val His Arg Pro His Val Glu Ser Gln Lys
  1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 10

Ser Tyr Gln His Asp Leu Arg Ala Tyr Gly Phe Trp Arg Leu Lys
  1               5                  10                  15

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 11

Cys Tyr Gly Gly
  1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
```

-continued

```
<222> LOCATION: 2,3
<223> OTHER INFORMATION: Xaa = any animo acid

<400> SEQUENCE: 12

Leu Xaa Xaa Cys
  1
```